(12) United States Patent
Chao et al.

(10) Patent No.: US 8,007,516 B2
(45) Date of Patent: Aug. 30, 2011

(54) INSTRUMENTS AND METHODS FOR MANIPULATING VERTEBRA

(75) Inventors: Nam T. Chao, Marlborough, MA (US); Dennis Hubbard, Lancaster, MA (US); Chris Rybicki, Fall River, MA (US); Ronald Sacher, Needham, MA (US); James R. Donahue, East Falmouth, MA (US); Simon Siu, Quincy, MA (US); Randal Betz, Ocean City, NJ (US)

(73) Assignee: DePuy Spine, Inc., Raynham, MA (US)

( * ) Notice: Subject to any disclaimer, the term of this patent is extended or adjusted under 35 U.S.C. 154(b) by 1183 days.

(21) Appl. No.: 11/707,471

(22) Filed: Feb. 16, 2007

(65) Prior Publication Data

US 2007/0162009 A1    Jul. 12, 2007

Related U.S. Application Data

(62) Division of application No. 11/073,352, filed on Mar. 4, 2005, now Pat. No. 7,951,175.

(51) Int. Cl.
*A61B 17/70* (2006.01)
(52) U.S. Cl. ...................................... 606/246
(58) Field of Classification Search ............. 606/57, 606/96, 104, 246
See application file for complete search history.

(56) References Cited

U.S. PATENT DOCUMENTS

| | | | |
|---|---|---|---|
| 2,669,896 A | 2/1954 | Clough |
| 2,952,285 A | 9/1960 | Roosli |
| 3,604,487 A | 9/1971 | Gilbert |
| 4,363,250 A | 12/1982 | Suga |
| 4,733,657 A | 3/1988 | Kluger |
| 4,743,260 A | 5/1988 | Burton |
| 4,887,596 A | 12/1989 | Sherman |
| 4,957,495 A | 9/1990 | Kluger |
| 4,987,892 A | 1/1991 | Krag et al. |
| 5,005,562 A | 4/1991 | Cotrel et al. |
| 5,067,955 A | 11/1991 | Cotrel |
| 5,092,866 A | 3/1992 | Breard et al. |
| 5,120,171 A | 6/1992 | Lasner |
| 5,176,678 A | 1/1993 | Tsou |

(Continued)

FOREIGN PATENT DOCUMENTS

DE    3923996 A1    1/1991

(Continued)

OTHER PUBLICATIONS

Wiltse, Leon L., "History of Pedicle Screw Fixation of the Spine" *Spine, Pedicle Fixation of the Lumbar Spine*, David M. Arnold and John E. Lonstein eds., Hanley & Belfus, Inc., vol. 6(1):1-10 (1992).

(Continued)

*Primary Examiner* — Nicholas Woodall
(74) *Attorney, Agent, or Firm* — Nelson Mullins Riley & Scarborough LLP

(57) ABSTRACT

A method for manipulating a vertebra includes connecting a first bone anchor to a first vertebra, connecting a second bone anchor to a second bone anchor, positioning a spinal rod in a receiving member of the first bone anchor and in a receiving member of the second bone anchor, connecting a first instrument to the receiving member of the first bone anchor, and manipulating the first instrument to rotate first bone anchor and the first vertebra relative to the second vertebra.

13 Claims, 17 Drawing Sheets

U.S. PATENT DOCUMENTS

| | | | |
|---|---|---|---|
| 5,176,680 A | 1/1993 | Vignaud et al. | |
| 5,181,917 A | 1/1993 | Rogozinski | |
| 5,181,971 A | 1/1993 | Ohtsuka | |
| 5,190,543 A | 3/1993 | Schlapfer | |
| 5,219,349 A | 6/1993 | Krag | |
| 5,226,766 A | 7/1993 | Lasner | |
| 5,263,939 A * | 11/1993 | Wortrich | 604/174 |
| 5,282,801 A | 2/1994 | Sherman | |
| 5,282,863 A | 2/1994 | Burton | |
| 5,330,474 A | 7/1994 | Lin | |
| 5,360,431 A | 11/1994 | Puno et al. | |
| 5,385,565 A | 1/1995 | Ray | |
| 5,387,213 A | 2/1995 | Breard et al. | |
| 5,415,661 A | 5/1995 | Holmes | |
| 5,468,241 A | 11/1995 | Metz-Stavenhagen et al. | |
| 5,487,744 A | 1/1996 | Howland | |
| 5,499,983 A | 3/1996 | Hughes | |
| 5,501,684 A | 3/1996 | Schlapfer et al. | |
| 5,520,689 A | 5/1996 | Schlapfer et al. | |
| 5,536,127 A | 7/1996 | Pennig | |
| 5,536,268 A | 7/1996 | Griss | |
| 5,540,688 A | 7/1996 | Navas | |
| 5,549,608 A | 8/1996 | Errico et al. | |
| 5,591,166 A | 1/1997 | Bernhardt et al. | |
| 5,649,931 A | 7/1997 | Bryant et al. | |
| 5,667,513 A | 9/1997 | Torrie et al. | |
| 5,672,176 A | 9/1997 | Biedermann et al. | |
| 5,797,911 A | 8/1998 | Sherman et al. | |
| 5,879,350 A | 3/1999 | Sherman et al. | |
| 5,882,350 A | 3/1999 | Ralph et al. | |
| 5,885,285 A | 3/1999 | Simonson | |
| RE36,221 E | 6/1999 | Breard et al. | |
| 5,910,141 A | 6/1999 | Morrison | |
| 5,951,555 A | 9/1999 | Rehak et al. | |
| 5,964,760 A | 10/1999 | Richelsoph | |
| 5,989,250 A | 11/1999 | Wagner et al. | |
| 5,989,254 A | 11/1999 | Katz | |
| 6,050,997 A | 4/2000 | Mullane | |
| 6,063,090 A | 5/2000 | Schlapfer | |
| 6,074,391 A | 6/2000 | Metz-Stavenhagen et al. | |
| 6,090,110 A | 7/2000 | Metz-Stavenhagen | |
| 6,090,113 A * | 7/2000 | Le Couedic et al. | 606/914 |
| 6,139,549 A | 10/2000 | Keller | |
| 6,146,383 A | 11/2000 | Studer et al. | |
| 6,183,472 B1 | 2/2001 | Lutz et al. | |
| 6,204,060 B1 | 3/2001 | Mehtali et al. | |
| 6,254,602 B1 | 7/2001 | Justis | |
| 6,261,287 B1 | 7/2001 | Metz-Stavenhagen | |
| 6,280,442 B1 | 8/2001 | Barker | |
| 6,280,443 B1 | 8/2001 | Gu et al. | |
| 6,302,888 B1 | 10/2001 | Mellinger et al. | |
| 6,309,389 B1 | 10/2001 | Baccelli | |
| 6,368,321 B1 | 4/2002 | Jackson | |
| 6,379,357 B1 | 4/2002 | Bernstein et al. | |
| 6,423,065 B2 | 7/2002 | Ferree | |
| 6,440,133 B1 | 8/2002 | Beale et al. | |
| 6,440,137 B1 | 8/2002 | Horvath et al. | |
| 6,443,953 B1 | 9/2002 | Perra et al. | |
| 6,478,798 B1 | 11/2002 | Howland | |
| 6,540,748 B2 | 4/2003 | Lombardo | |
| 6,565,567 B1 | 5/2003 | Haider | |
| 6,597,279 B1 | 7/2003 | Haraguchi | |
| 6,623,485 B2 | 9/2003 | Doubler et al. | |
| 6,648,888 B1 | 11/2003 | Shluzas et al. | |
| 6,660,006 B2 | 12/2003 | Markworth et al. | |
| 6,689,137 B2 | 2/2004 | Reed | |
| 6,692,500 B2 | 2/2004 | Reed et al. | |
| 6,695,843 B2 | 2/2004 | Biedermann et al. | |
| 6,716,214 B1 | 4/2004 | Jackson | |
| 6,733,502 B2 | 5/2004 | Altarac et al. | |
| 6,743,231 B1 | 6/2004 | Gray et al. | |
| 6,749,613 B1 | 6/2004 | Conchy et al. | |
| 6,755,829 B1 | 6/2004 | Bono et al. | |
| 6,783,527 B2 | 8/2004 | Drewry et al. | |
| 6,800,078 B2 | 10/2004 | Reed et al. | |
| 6,800,079 B2 | 10/2004 | Reed et al. | |
| 6,837,889 B2 | 1/2005 | Shluzas | |
| 6,964,666 B2 | 11/2005 | Jackson | |
| 7,179,261 B2 | 2/2007 | Sicvol et al. | |
| 7,322,979 B2 | 1/2008 | Crandall et al. | |
| 7,455,685 B2 | 11/2008 | Justis | |
| 7,465,306 B2 | 12/2008 | Pond, Jr. et al. | |
| 7,666,189 B2 | 2/2010 | Gerber et al. | |
| 7,766,944 B2 | 8/2010 | Metz-Stavenhagen | |
| 2001/0020169 A1 | 9/2001 | Metz-Stavenhagen | |
| 2002/0035366 A1 | 3/2002 | Walder et al. | |
| 2002/0082599 A1 | 6/2002 | Crandall et al. | |
| 2002/0133155 A1 | 9/2002 | Ferree | |
| 2002/0143341 A1 | 10/2002 | Biedermann et al. | |
| 2002/0173789 A1 | 11/2002 | Howland | |
| 2003/0073995 A1 | 4/2003 | Reed | |
| 2003/0083657 A1 | 5/2003 | Drewry et al. | |
| 2003/0088248 A1 | 5/2003 | Reed | |
| 2003/0100896 A1 | 5/2003 | Biedermann et al. | |
| 2003/0105460 A1 | 6/2003 | Crandall et al. | |
| 2003/0109880 A1 | 6/2003 | Shirado et al. | |
| 2003/0171749 A1 | 9/2003 | Le Couedic et al. | |
| 2003/0176861 A1 | 9/2003 | Reed | |
| 2003/0191470 A1 | 10/2003 | Ritland | |
| 2003/0203488 A1 | 10/2003 | Mehtali et al. | |
| 2003/0220642 A1 | 11/2003 | Freudiger | |
| 2003/0220643 A1 | 11/2003 | Ferree | |
| 2004/0002708 A1 | 1/2004 | Ritland | |
| 2004/0049189 A1 | 3/2004 | Le Couedic et al. | |
| 2004/0049190 A1 | 3/2004 | Biedermann et al. | |
| 2004/0073215 A1 | 4/2004 | Carli | |
| 2004/0147937 A1 | 7/2004 | Dunbar et al. | |
| 2004/0158258 A1 | 8/2004 | Bonati et al. | |
| 2004/0172025 A1 | 9/2004 | Drewry et al. | |
| 2004/0181224 A1 | 9/2004 | Biedermann et al. | |
| 2004/0186473 A1 | 9/2004 | Cournoyer et al. | |
| 2004/0204711 A1 | 10/2004 | Jackson | |
| 2004/0225289 A1 | 11/2004 | Biedermann et al. | |
| 2004/0267260 A1 | 12/2004 | Mack et al. | |
| 2004/0267275 A1 | 12/2004 | Cournoyer et al. | |
| 2005/0033291 A1 | 2/2005 | Ebara | |
| 2005/0033295 A1 | 2/2005 | Wisnewski | |
| 2005/0065514 A1 | 3/2005 | Studer | |
| 2005/0065515 A1 | 3/2005 | Jahng | |
| 2005/0065516 A1 | 3/2005 | Jahng | |
| 2005/0070917 A1 | 3/2005 | Justis | |
| 2005/0085815 A1 | 4/2005 | Harms et al. | |
| 2005/0131408 A1 | 6/2005 | Sicvol et al. | |
| 2005/0131422 A1 | 6/2005 | Anderson et al. | |
| 2005/0159650 A1 * | 7/2005 | Raymond et al. | 600/201 |
| 2005/0192573 A1 | 9/2005 | Abdelgany et al. | |
| 2005/0192589 A1 | 9/2005 | Raymond et al. | |
| 2005/0222570 A1 | 10/2005 | Jackson | |
| 2005/0228376 A1 | 10/2005 | Boomer et al. | |
| 2005/0245928 A1 * | 11/2005 | Colleran et al. | 606/61 |
| 2005/0261687 A1 | 11/2005 | Garamszegi et al. | |
| 2005/0283244 A1 | 12/2005 | Gordon | |
| 2005/0288668 A1 | 12/2005 | Brinkhaus | |
| 2006/0036255 A1 | 2/2006 | Pond et al. | |
| 2006/0149236 A1 | 7/2006 | Barry | |
| 2006/0155277 A1 | 7/2006 | Metz-Stavenhagen | |
| 2006/0173454 A1 | 8/2006 | Spitler et al. | |
| 2006/0195092 A1 | 8/2006 | Barry | |
| 2006/0200131 A1 | 9/2006 | Chao et al. | |
| 2006/0200132 A1 | 9/2006 | Chao et al. | |
| 2006/0217735 A1 | 9/2006 | MacDonald et al. | |
| 2006/0229614 A1 | 10/2006 | Foley et al. | |
| 2007/0162009 A1 | 7/2007 | Chao et al. | |
| 2007/0162010 A1 | 7/2007 | Chao et al. | |
| 2008/0195159 A1 | 8/2008 | Kloss et al. | |

FOREIGN PATENT DOCUMENTS

| | | |
|---|---|---|
| DE | 4107480 A1 | 9/1992 |
| DE | 10005385 A1 | 8/2001 |
| DE | 10005386 A1 | 8/2001 |
| DE | 20207851 U1 | 11/2002 |
| EP | 0328883 B1 | 8/1989 |
| EP | 0381588 B2 | 8/1990 |
| EP | 0441729 B1 | 8/1991 |
| EP | 0487895 A1 | 6/1992 |
| EP | 0558883 B1 | 9/1993 |
| EP | 0572790 B1 | 12/1993 |

| | | | |
|---|---|---|---|
| EP | 0592266 A1 | 4/1994 |
| EP | 0669109 B1 | 8/1995 |
| EP | 0784693 B1 | 7/1997 |
| EP | 0880344 B1 | 12/1998 |
| EP | 0885598 A2 | 12/1998 |
| EP | 0951246 B1 | 10/1999 |
| EP | 1023873 A2 | 8/2000 |
| EP | 1090595 A2 | 4/2001 |
| EP | 1295566 A1 | 3/2003 |
| EP | 1364622 B1 | 11/2003 |
| WO | WO-90/02527 A1 | 3/1990 |
| WO | WO-9822033 A1 | 5/1998 |
| WO | 98/25534 A1 | 6/1998 |
| WO | WO-9944527 A1 | 9/1999 |
| WO | WO-01/45576 A1 | 6/2001 |
| WO | WO-02/07622 A1 | 1/2002 |
| WO | WO-02/102259 A2 | 12/2002 |
| WO | WO-03/007828 A1 | 1/2003 |
| WO | WO-03/032863 A2 | 4/2003 |
| WO | WO-03/049629 A1 | 6/2003 |
| WO | WO2004/019755 A2 | 3/2004 |
| WO | WO-2004/034916 A1 | 4/2004 |
| WO | WO-2005/013839 A2 | 2/2005 |
| WO | WO-2005/030065 A1 | 4/2005 |
| WO | WO-2005/044117 A2 | 5/2005 |
| WO | WO 2005/044123 A1 | 5/2005 |

OTHER PUBLICATIONS

European Office Action for Application No. 06736870, dated Dec. 18, 2009.
International Search Report for Application No. PCT/US06/05811, dated Sep. 13, 2007.
Wiltse, Leon L. et al., "History of Pedicle Screw Fixation of the Spine," *Spine, State of the Art Reviews*, vol. 6(1):1-10 (1992).
International Search Report and Written Opinion for Application No. PCT/US06/40621, dated May 18, 2007.
European Office Action for Application No. 06735464.7, dated Apr. 14, 2010.

* cited by examiner

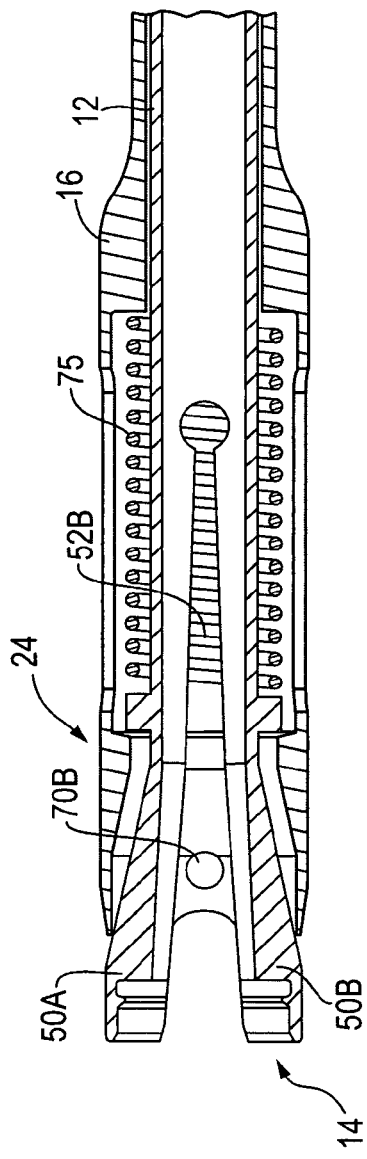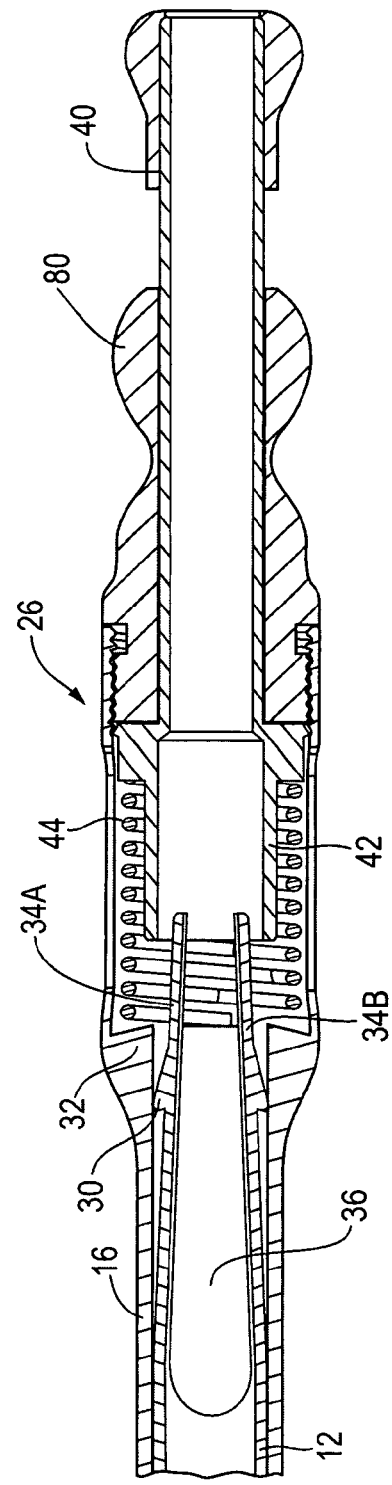

FIG. 15
FIG. 16
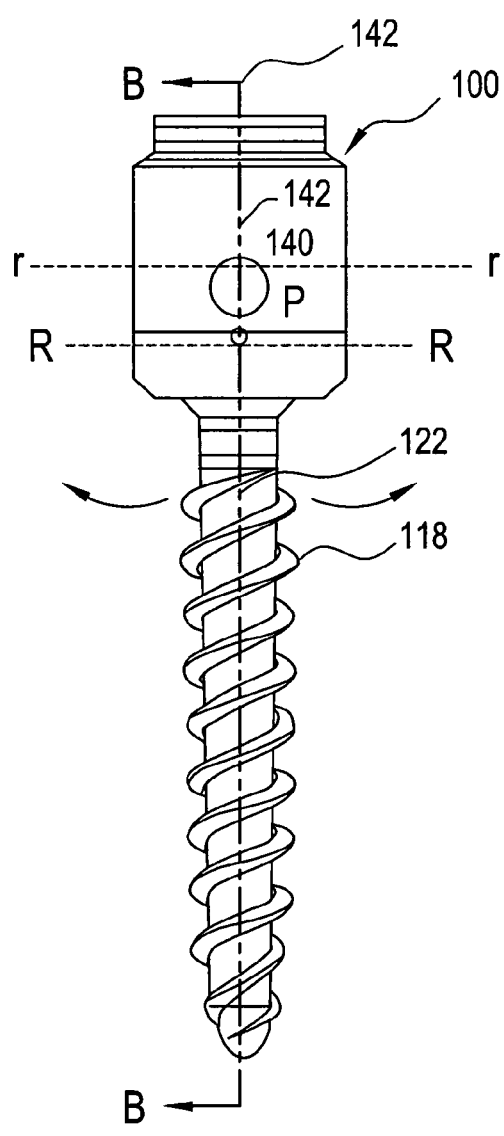
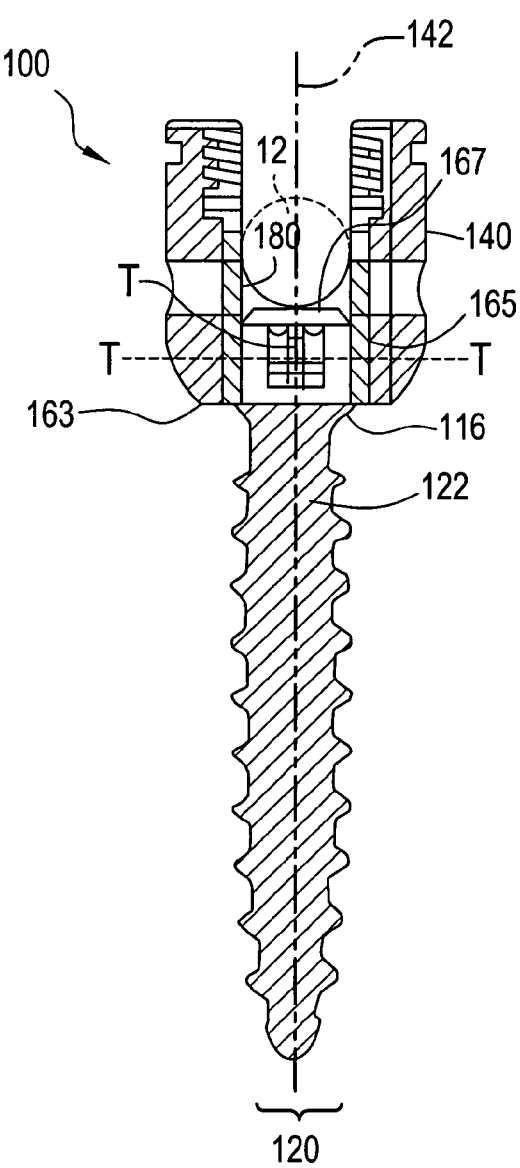

FIG. 17A
FIG. 17B
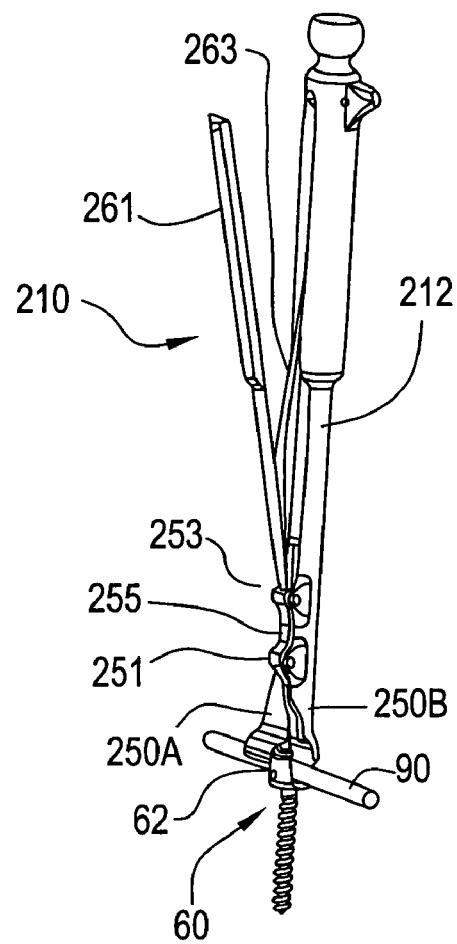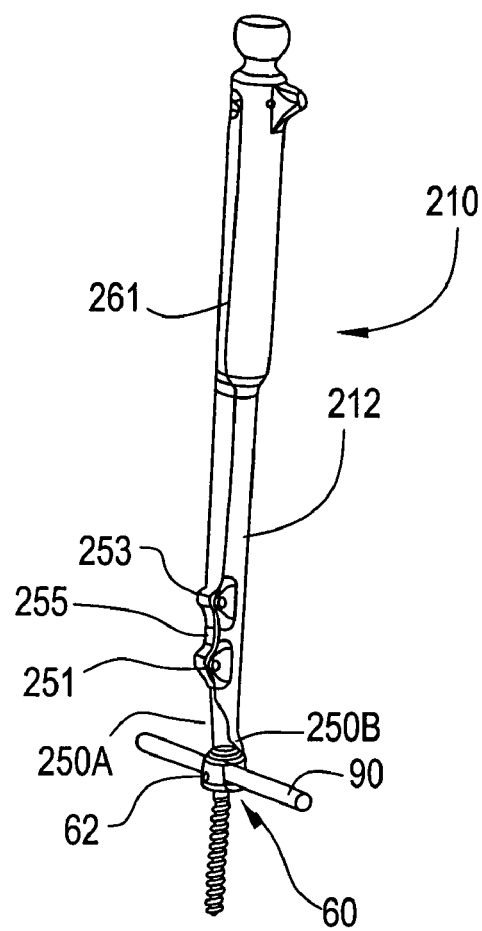

INSTRUMENTS AND METHODS FOR MANIPULATING VERTEBRA

CROSS-REFERENCE TO RELATED APPLICATIONS

This application is a divisional application of U.S. Ser. No. 11/073,352, filed Mar. 4, 2005, the contents of which are incorporated herein.

BACKGROUND

In spinal deformity surgical procedures, the curvature of the spine, for example, the coronal curvature and/or the sagittal curvature of the spine, can be corrected by the implantation of a construct of bone anchors (e.g., hooks or bone screws) and spinal fixation elements (e.g., rods or tethers). In addition to correcting the curvature of the spine, the angular relationship of one or more vertebrae relative to other vertebrae may also be corrected. Conventional surgical procedures for corrected the angular relationship of a vertebra involve rotating the spinal fixation element, for example, a spinal rod, connected to the vertebra by a bone anchor. In the case of constructs including a spinal rod, this procedure is typically referred to as rod derotation. Rod derotation can place significant stress on the interface between the bone anchors connected to the rotated spinal rod and the vertebra in which each bone anchor is implanted. This stress can cause a failure of one or more of the bone anchors or vertebrae. Accordingly, there is a need for improved instruments and methods for manipulating, e.g., rotating a vertebra.

SUMMARY

Disclosed herein are instruments and methods for manipulating a vertebra. The instruments and methods disclosed herein are particularly suited to facilitate rotation of a vertebra relative to another vertebra to correct the angular relationship of the vertebrae.

In accordance with one exemplary embodiment, an instrument for manipulating a vertebra may comprise an inner shaft having a proximal end, a distal end and a lumen extending between the proximal end and the distal end, a pair of fingers disposed at the distal end of the inner shaft, and an outer sleeve disposed about the inner shaft. The inner shaft, in the exemplary embodiment, may be movable relative to the outer sleeve between a first position in which the fingers are advanced beyond a distal end of the outer sleeve and a second position in which a substantial portion of the fingers are disposed within the sleeve. The fingers, when in the first position, may be configured to capture a spinal rod receiving member of the bone anchor therebetween to permit rotation of the bone anchor and a vertebra in which the bone anchor is engaged by manipulation of the instrument.

In accordance with another exemplary embodiment, a system for manipulating one or more vertebra may comprise a first instrument having a distal end configured to engage a first bone anchor connected to a first vertebra, a second instrument having a distal end configured to engage a second bone anchor connected to a second vertebra, and a connector connecting the first instrument and the second instrument. The connector, in the exemplary embodiment, may include a first receiving element for receiving the first instrument and a second receiving element for receiving the second instrument. The first receiving element may be adjustable relative to the second receiving element.

In accordance with another exemplary embodiment, a method for manipulating a vertebra may comprise connecting a first bone anchor to a first vertebra, connecting a second bone anchor to a second bone anchor, positioning a spinal rod in a receiving member of the first bone anchor and in a receiving member of the second bone anchor, connecting a first instrument to the receiving member of the first bone anchor, and manipulating the first instrument to rotate first bone anchor and the first vertebra relative to the second vertebra.

In accordance with another exemplary embodiment, a method for manipulating a vertebra may comprise engaging a first bone anchor to a first vertebra, the receiving member of the first bone anchor being adjustable relative to a bone engaging shaft of the first bone anchor in a first direction and restricted from motion in a second direction, connecting a first instrument to the receiving member of the first bone anchor, and moving the first instrument in a direction approximately parallel to the second direction to manipulate first bone anchor and the first vertebra.

BRIEF DESCRIPTION OF THE FIGURES

These and other features and advantages of the instruments and methods disclosed herein will be more fully understood by reference to the following detailed description in conjunction with the attached drawings in which like reference numerals refer to like elements through the different views. The drawings illustrate principles of the instruments and methods disclosed herein and, although not to scale, show relative dimensions.

FIGS. 5A-5C are side elevational views in cross section of the instrument of FIG. 1, illustrating the instrument in the second position;

FIG. 15 is a side elevation view of the bone anchor of FIG. 14;

FIG. 16 is a side elevation view in cross section of the bone anchor of FIG. 14, taken along the line B-B of FIG. 15; and FIGS. 17A and 17B are perspective views of an exemplary embodiment of an instrument for manipulating a vertebra, illustrating the instrument in a first position for capturing a bone anchor (FIG. 17A) and a second position for retaining the bone anchor (FIG. 17B).

DETAIL DESCRIPTION OF EXEMPLARY EMBODIMENTS

Figure 1:
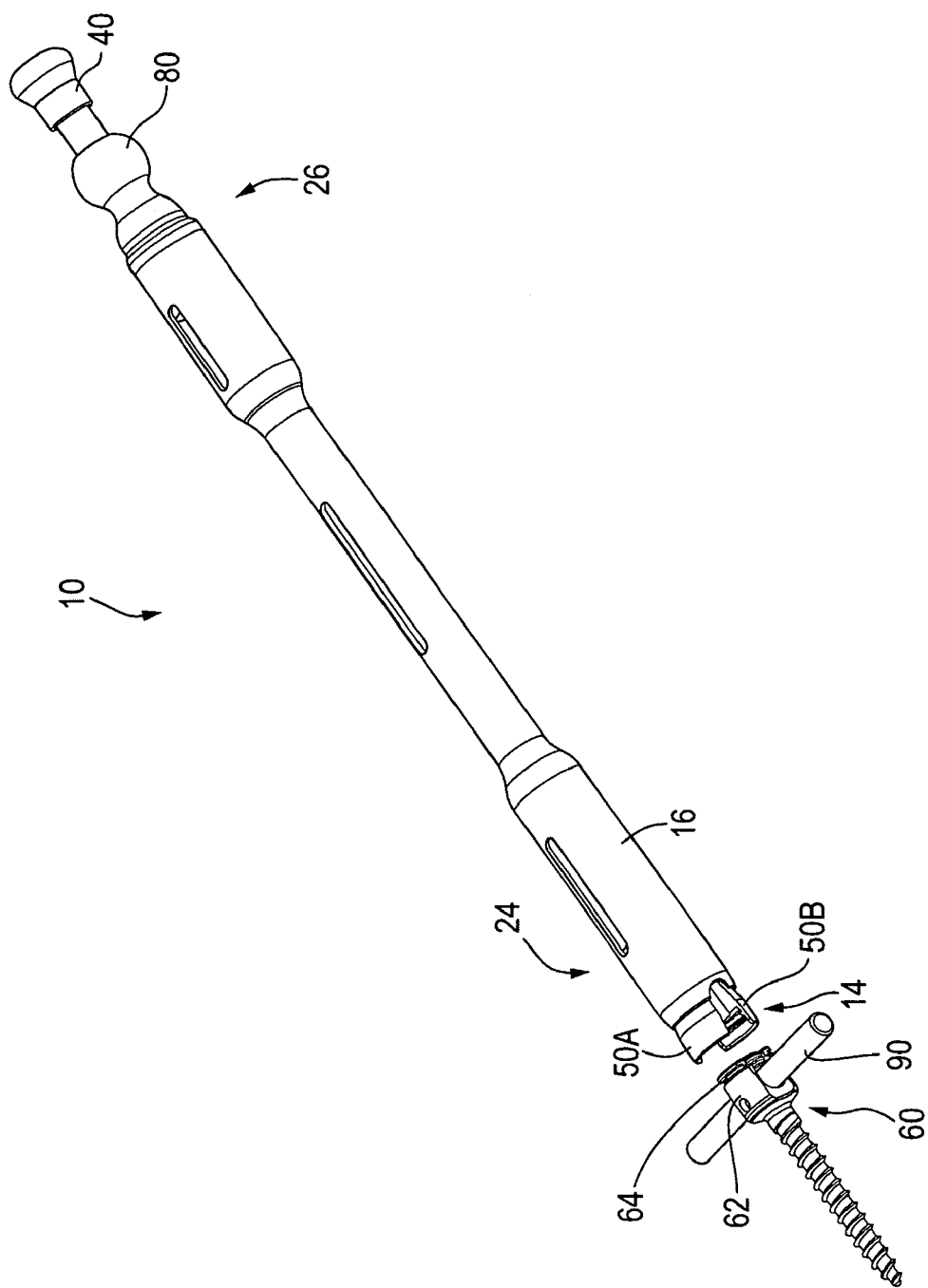
FIG. 1 is a perspective view of an exemplary embodiment of an instrument for manipulating a vertebra, illustrating the instrument in a first position for engaging a bone anchor.
Figure 2:
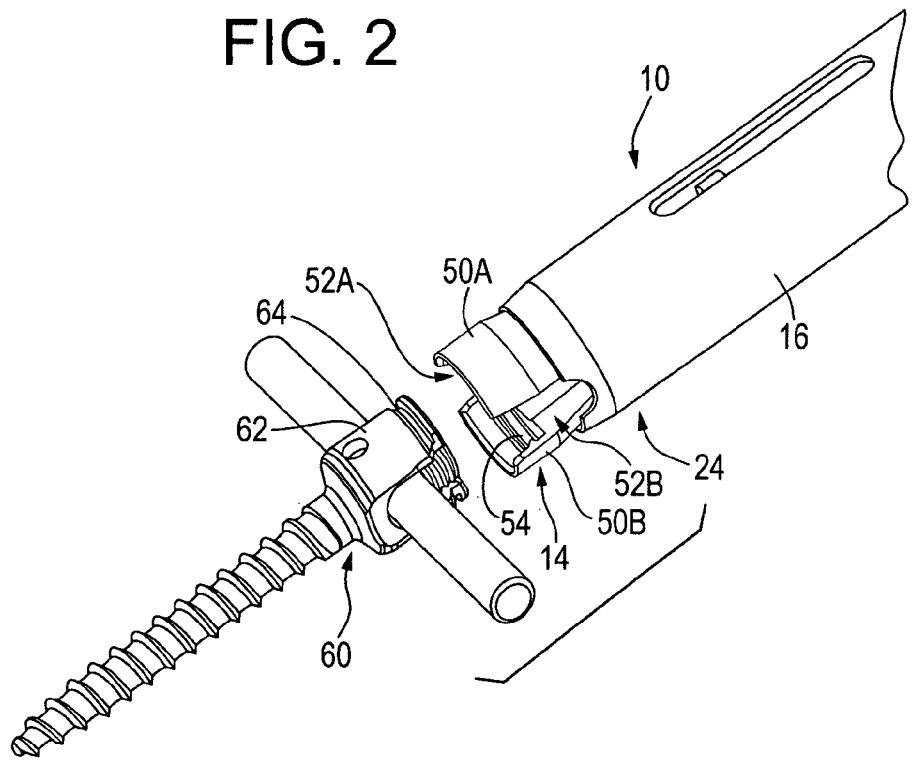
FIG. 2 is a perspective view of the distal end of the instrument of FIG. 1, illustrating the instrument in the first position for engaging a bone anchor.
Figure 3:
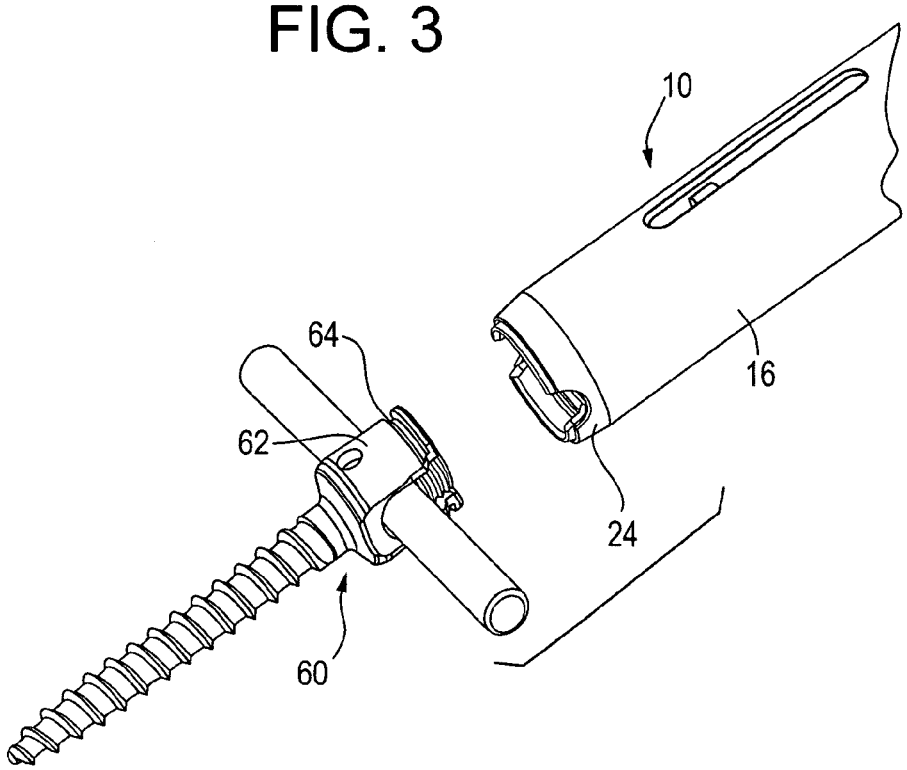
FIG. 3 is a perspective view of the distal end of the instrument of FIG. 1, illustrating the instrument in a second position.

Certain exemplary embodiments will now be described to provide an overall understanding of the principles of the structure, function, manufacture, and use of the instruments and methods disclosed herein. One or more examples of these embodiments are illustrated in the accompanying drawings. Those of ordinary skill in the art will understand that the instruments and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The articles "a" and "an" are used herein to refer to one or to more than one (i.e. to at least one) of the grammatical object of the article. By way of example, "an element" means one element or more than one element.

The terms "comprise," "include," and "have," and the derivatives thereof, are used herein interchangeably as comprehensive, open-ended terms. For example, use of "comprising," "including," or "having" means that whatever element is comprised, had, or included, is not the only element encompassed by the subject of the clause that contains the verb.

FIGS. 1-6 illustrate an exemplary embodiment of an instrument 10 for manipulating a vertebra. The exemplary instrument 10 includes an inner shaft 12, an implant engagement mechanism 14 disposed at the distal end 18 of the inner shaft 12, and an outer sleeve 16 disposed about the inner shaft 12. The exemplary instrument 10 may be employed to engage a bone anchor 60 implanted in a vertebra and maneuver the bone anchor 60 and the vertebra by manipulating the instrument 10. For example, the exemplary instrument 10 may be employed to rotate the bone anchor 60 and the vertebra relative to other vertebrae and thereby by correct the angular orientation of the vertebra. The instrument 10, when employed in the exemplary manner, thus may be used to effect segmental correction of the angular orientation of the vertebrae of the spine.

The inner shaft 12 of the exemplary instrument 10 may have a distal end 18, a proximal end 20, and a lumen 22 extending between the proximal end 20 and the distal end 18. In the exemplary embodiment, the inner shaft 12 is generally tubular in shape having an approximately circular cross section. One skilled in the art will appreciate that the inner shaft 12 may have other cross sectional shapes including elliptical or rectilinear. The lumen 22 of the inner shaft 12 may be sized to receive an instrument, such as a screw driver or the like, therethrough. The outer sleeve 16 of the exemplary instrument 10 is disposed about the inner shaft 12 and may have a distal end 24, a proximal end 26, and a lumen 28 extending between the proximal end 26 and the distal end 24. The outer sleeve 16 and the inner shaft 12 may have complementary shapes to facilitate positioning of the inner shaft 12 within the outer sleeve 16. For example, in the illustrated embodiment, the outer sleeve is generally tubular in shape have an approximately circular cross section and the longitudinal axis of the elongate shaft 12 is coincident with the longitudinal axis of the outer sleeve 16. The inner shaft 12 may be disposed within the lumen 28 of the outer sleeve 16 and may be movable within the lumen 28 relative to the outer sleeve 16. For example, the inner shaft 12 may be movable along the longitudinal axis of the outer sleeve 16.

Figure 4A:
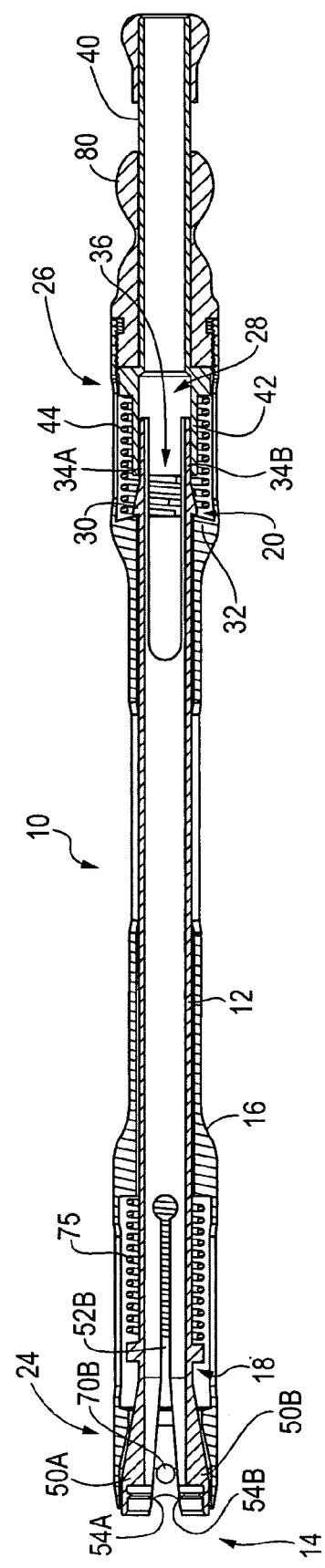
FIGS. 4A-4C are side elevational views in cross section of the instrument of FIG. 1, illustrating the instrument in the first position.
Figure 4B:
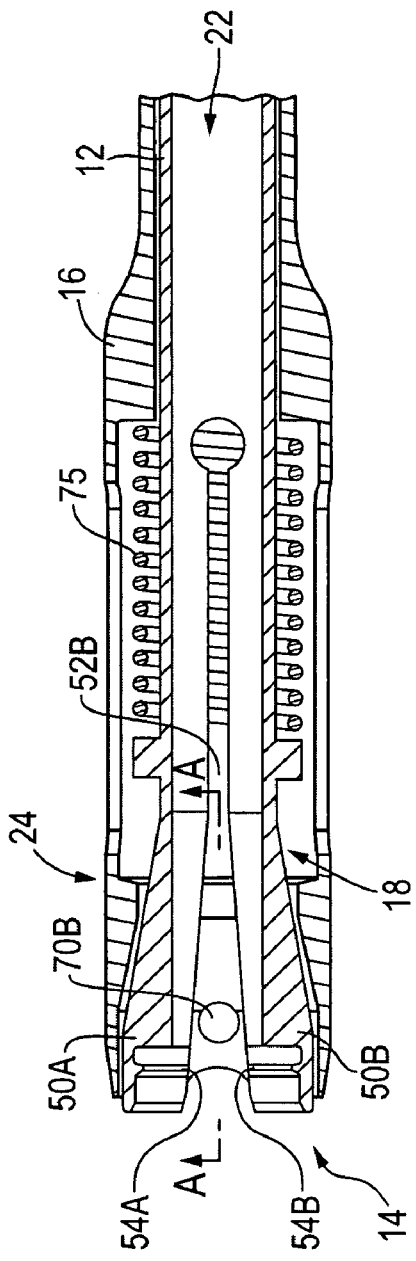
Figure 4C:
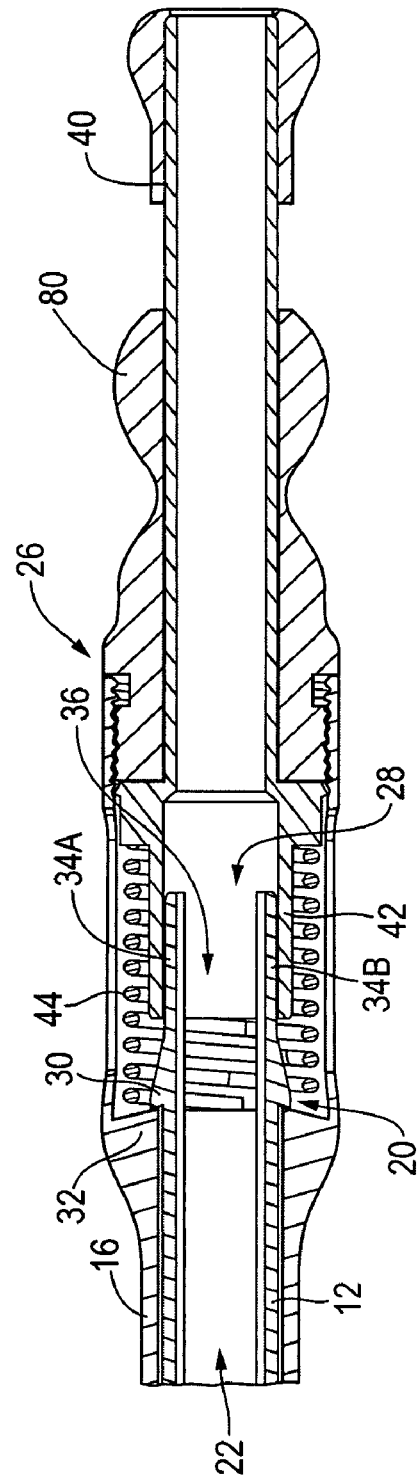
Figure 5A:
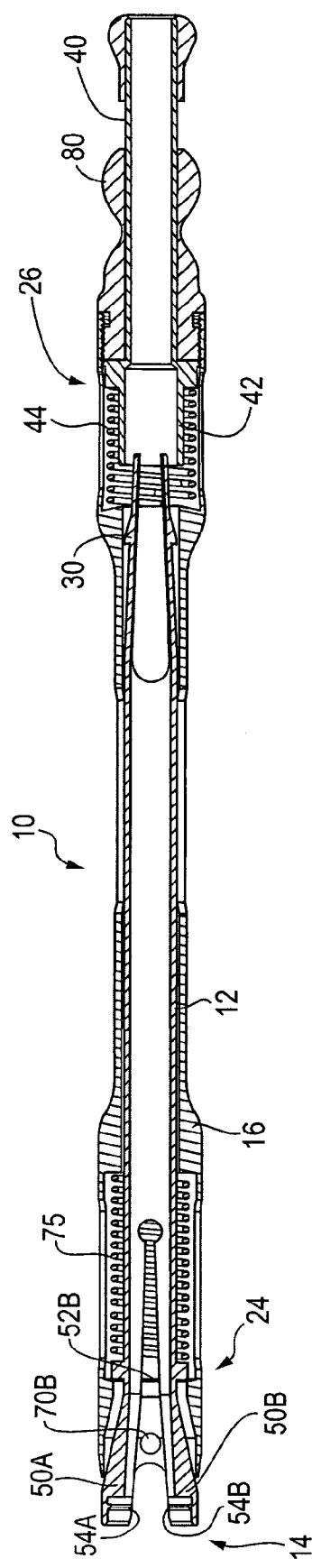
Figure 6:
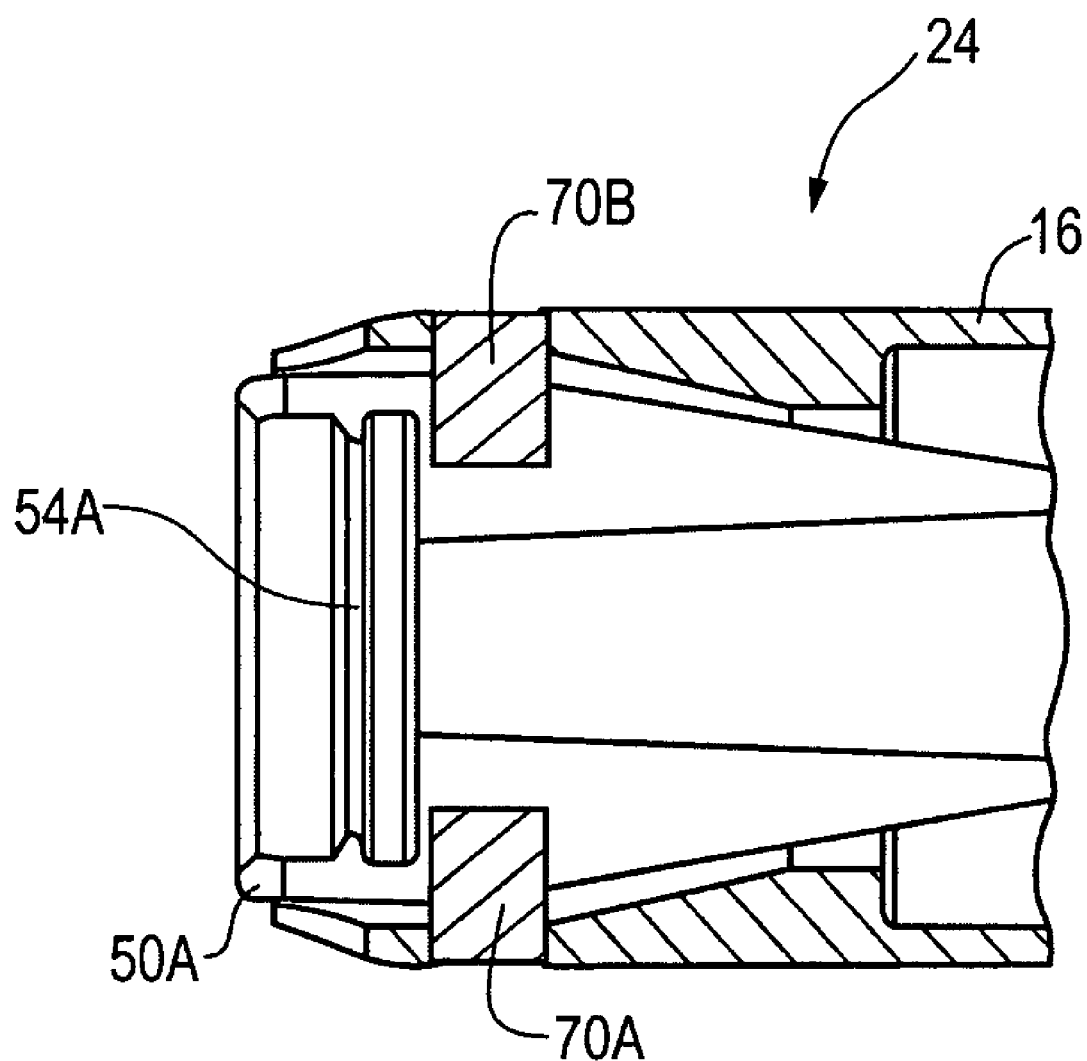
FIG. 6 is a side elevational view in cross section of the distal end of the instrument of FIG. 1 taken along the line A-A of FIG. 4B.

The proximal end 20 of the inner shaft 12 may include a mechanism to retain the inner shaft 12 in a position relative to the outer sleeve 16. For example, in the exemplary embodiment, an annular ridge 30 may be provided proximate the proximal end 20 of the inner shaft 12 or at other locations along the length of the shaft 12. The annular ridge 30 may be an increased diameter segment of the shaft 12 that is sized, shaped, and positioned to engage a shoulder 32 provided within the lumen 28 of the outer sleeve 16 and maintain the inner shaft 12 in a predetermined position relative to the outer sleeve 16. The shoulder 32 may be annular in shape and may be defined by a narrowing of the inner diameter of the lumen 28 of the sleeve 16. The shoulder 32 may have a sloped outer surface to minimize the effect of wear on the shoulder 32. In the exemplary embodiment, the annular ridge 30 may be selectively engaged and disengaged to permit the inner shaft 12 to be selectively moved relative to the outer sleeve 16. For example, the proximal end 20 of the inner shaft 12 may be moved between an increased diameter configuration, in which the ridge 30 engages the shoulder 32 to maintain the inner shaft 12 in position relative to the outer sleeve 16, as illustrated in FIGS. 4A-C, and a decreased diameter configuration, in which the ridge 30 disengages the shoulder 32 to permit the inner shaft 12 to move relative to the outer sleeve 16, as illustrated in FIGS. 5A-C. In the exemplary embodiment, the proximal end 20 of the inner shaft 12 is generally U-shaped in cross section having a pair of tabs 34A, 34B spaced apart by a slot 36. The tabs 34A, 34B may be compressed toward one another to facilitate movement of the proximal end 28 of the inner shaft 12 from the increase diameter configuration to the decreased diameter configuration. The tabs 34A, 34B may be biased to the increased diameter configuration in which the tabs 34A, 34B are positioned generally parallel to one another.

The exemplary instrument 10 may include a plunger 40 positioned within the outer sleeve 16 at the proximal end 26 of the outer sleeve 16. The plunger 40, in the exemplary embodiment, is engageable with the proximal end 20 of the inner shaft 12 and is operable to move inner shaft 12 relative to the outer sleeve 16. In the exemplary embodiment, the plunger 40 may have a distal end 42 configured to move the proximal end 20 of the inner shaft 12 from the increased diameter configuration to the decreased diameter configuration. For example, the distal end 42 of the plunger 40 may be generally cylindrical in shape and may have an inner diameter less than the diameter of the annular ridge 30. In operation, the plunger 40 may be advanced from a proximal position, illustrated in FIGS. 4A-C, to a distal position in which the distal end 42 is advanced about the proximal end 20 of the inner shaft 12 to engage the annular ridge 30 and compress the tabs 34A, 34B towards one another. The annular ridge 30 may have a sloped outer surface to facilitate engagement with the proximal end 42 of the plunger 40 and translation of the proximal end 28 from the increased diameter configuration to the decreased diameter configuration. The instrument 10 may include a proximal spring 44 positioned between the outer sleeve 12 and the plunger 40 to bias the plunger 40 to a proximal position.

One skilled in the art will appreciate that other mechanisms for moving the inner shaft 12 relative to the outer sleeve 16 may be employed. For example, the outer sleeve 16 may include external threads for connecting with an internally threaded collar. The collar may engage the inner shaft to advance and/or retract the inner shaft 12 by rotation of the collar about the outer sleeve 16.

The exemplary instrument 10 includes an implant engagement mechanism 14 configured to engage a bone anchor 60, such as, for example, a hook, a monoaxial bone screw, or a polyaxial bone screw, and thereby by connect the instrument to the bone anchor 60 in a manner sufficient to permit manipulation of the bone anchor and the vertebra in which the bone anchor is implanted. In the exemplary embodiment, the implant engagement mechanism 14 is a pair of fingers 50A,B at the distal end 18 of the inner shaft 12. In the exemplary embodiment, the fingers 50A and 50B are defined by the sidewalls of the inner tube 12 and are separated by slots 52A and 52B. In certain exemplary embodiments, fingers 50A and 50B may be flexible and resilient in the radial direction to facilitate connection to a bone anchor. For example, the fingers 50A and 50B may be flexed apart in the radial direction from a first, relaxed position to facilitate advancement of the fingers longitudinally over a portion of the bone anchor. Once positioned about a portion of the bone anchor, the fingers 50A and 50B may provide a radially compressive force on the bone anchor as the fingers 50A and 50B attempt to return to the first, relaxed position. In other exemplary embodiments, including the exemplary instrument 10, the fingers 50A and 50B need not be flexible and resilient.

The inner shaft 12, in the exemplary embodiment, may be movable relative to the outer sleeve 16 between a first, distal position in which the fingers 50A, 50B are advanced beyond a distal end 24 of the outer sleeve 16, as illustrated in FIGS. 1, 2, and 4A-4C, and a second, proximal position in which a substantial portion of the fingers 50A, B are disposed within the sleeve 16, as illustrated in FIGS. 3 and 5A-C. The fingers 50A, 50C, when the inner shaft 12 is in the first position, may be configured to capture the bone anchor 60 therebetween. In the exemplary embodiment, for example, fingers 50A, 50B may move apart from one another when the inner shaft 12 is moved to the first position to facilitate positioning of the spinal rod receiving member 62 of the bone anchor 60, between the fingers 50A, 50B.

The fingers 50A, B, when the inner shaft 12 is moved to the second, proximal position, may move toward one another to retain the bone anchor 60 between the fingers 50A, 50B. The fingers 50A, 50B may be inhibited from separating by the outer sleeve 16 when the inner shaft is in the second, proximal position. The fingers 50A, 50B, when the inner shaft is in the second, proximal position are spaced apart a distance sufficient to retain the bone anchor between the fingers 50A, 50B. In the exemplary embodiment, for example, the bone anchor 60 is retained between the fingers 50A, 50B in a manner sufficient to permit maneuvering of the bone anchor and a vertebra in which the bone anchor is implanted by manipulation of the instrument. For example, the bone anchor 60 and vertebra may be rotated, moved along the axis of the instrument 10, and/or moved in a direction perpendicular to the axis to the instrument 10 by the instrument 10.

In the illustrated exemplary embodiment, each finger 50A and 50B may include one or more radially inward facing projection 54A, 54B that is sized and shaped to seat within an opening provided in a portion of the bone anchor to facilitate retention of the bone anchor 60 by the fingers 50A, 50B. The size, shape and number of projections can be varied depending on, for example, the opening(s) provided on the bone anchor and type of connection desired. In the illustrated exemplary embodiment, for example, each projection 54A, 54B is generally arcuate in shape and has a cross section that is complementary to an arcuate groove 64 provided in the spinal fixation element receiving member 62 of the exemplary bone anchor 60. An exemplary bone anchor having an arcuate groove to facilitate connection with an instrument is described in detail in U.S. patent application Ser. No. 10/738,286, filed Dec. 16, 2003, incorporated herein by reference.

In the exemplary embodiment, the outer sleeve 16 of the instrument 10 may include one or more projections 70 on the inner surface thereof. The projections 70 may be positioned at the distal end 24 of the outer sleeve 16 to facilitate separation of the fingers 50A, 50B as inner shaft 12, and, thus, the fingers 50A, 50B are moved to the first, distal position. In the exemplary embodiment, a pair of cylindrical shaped projections 70 are spaced diametrically opposed to one another at the distal end 24 of the outer sleeve 16. The projections 70A, 70B, in the exemplary embodiment, are positioned within the slots 52A, 52B, respectively. The slots 52A, 52B narrow in the proximal direction. Advancement of the projections 70A, 70B within the slots 52A, 52B causes the fingers 50A, 50B to separate.

In alternative exemplary embodiments, the projections 70A, 70B may not be provided. In such embodiments, the fingers 50A, 50B may remain approximately parallel to one another when the inner shaft 12 is advance to the first position. The fingers 50A, 50B may be rotated into engagement with the bone anchor by, for example, positioning the fingers 50A, 50B in the rod slots of the receiving member 62 of the bone anchor 60 and rotating the fingers 50A, 50B such that the projections 54A, 54B each engage a groove 64. Alternatively, the fingers 50A, 50B may be flexed apart as the fingers 50A, 50B engage the receiving member 62 and, as the inner shaft 12 is advanced distally relative to the receiving member 62, each projection 54A, 54B may snap into engagement with a groove 64.

The instrument 10 may include one or more springs to bias the inner shaft 12 to the first position or the second position. In the exemplary embodiment, for example, a distal spring 75 may engage the inner shaft 12 and the outer sleeve 16 to bias the inner shaft 12 to the first, distal position.

The exemplary instrument 10 may include a connection element configure to engage a connector, such as the exemplary connector 200 described below, for connecting the instrument 10 to another instrument, for example, another instrument for manipulating a vertebra. In the illustrated exemplary embodiment, for example the outer sleeve 16 includes a connection element 80 positioned at the proximal end 26 of the outer sleeve 16. The connection element 80 may be configured to permit polyaxial motion of the instrument 10 relative to the connector. For example, the connection element 80 of the exemplary embodiment may have be at least partially spherical in shape to engage a complementary shaped receiving element of the connector.

The exemplary instrument 10 may be constructed of any biocompatible material including, for example, metals, such as stainless steel or titanium, polymers, ceramics, or composites thereof. The length and diameter of the instrument 10 may vary depending on the area of the spine being treated (e.g., lumbar, thoracic, or cervical) and the approach (e.g., posterior, anterior, or lateral). For example, the length of the instrument 10 may be selected to at least span from a skin incision to proximate a vertebra. The diameter of the instrument 10 may be selected to facilitate positioning of the instrument 10 through an open incision or a minimally invasive incision. In certain exemplary embodiments, for example, the diameter of the instrument may be selected to facilitate delivery of the instrument 10 through a minimally invasive access device such as a cannula or expandable retractor.

FIGS. 7-10 illustrate an exemplary embodiment of a connector 200 for connecting two or more instruments and facilitating cooperative movement of the instruments. The exemplary connector 200 is particularly suited to connecting one or more instruments for manipulating a vertebra, such as the instrument 10 described above. One skilled in the art will appreciate, however, the connector 200 may be used to connect any type of spinal or surgical instruments.

The exemplary connector 200 may include a plurality of receiving elements 202, each of which connects to an instrument. Any number of the receiving elements 202 may be provided. In the illustrated exemplary embodiment, the connector 200 includes a first adjustable receiving element 202A for receiving a first instrument and a second receiving element 202B for receiving a second instrument. The first receiving element 202A and/or the second receiving element 202B may be adjustable relative to one another to facilitate connection to two spaced apart instruments. For example, in the illustrated exemplary embodiment, the first receiving element 202A is adjustable relative to the second receiving element 202B and the connector 200 and the second receiving element 202B is fixed relative to the connector 200.

Figure 7:
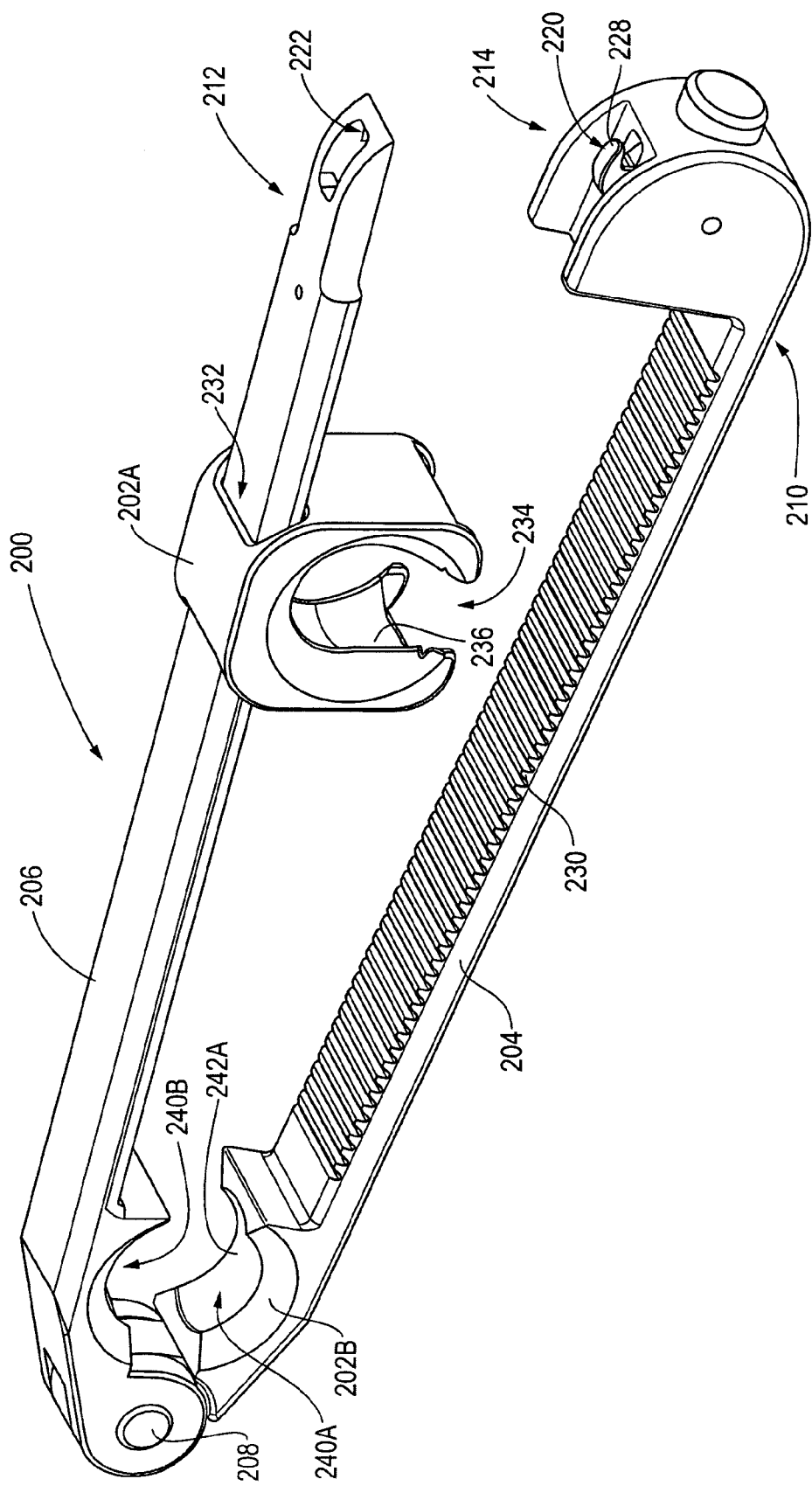
FIG. 7 is a perspective view of a connector for connecting two instruments, such as the instrument of FIG. 1, illustrating the connector in an open position.
Figure 8:
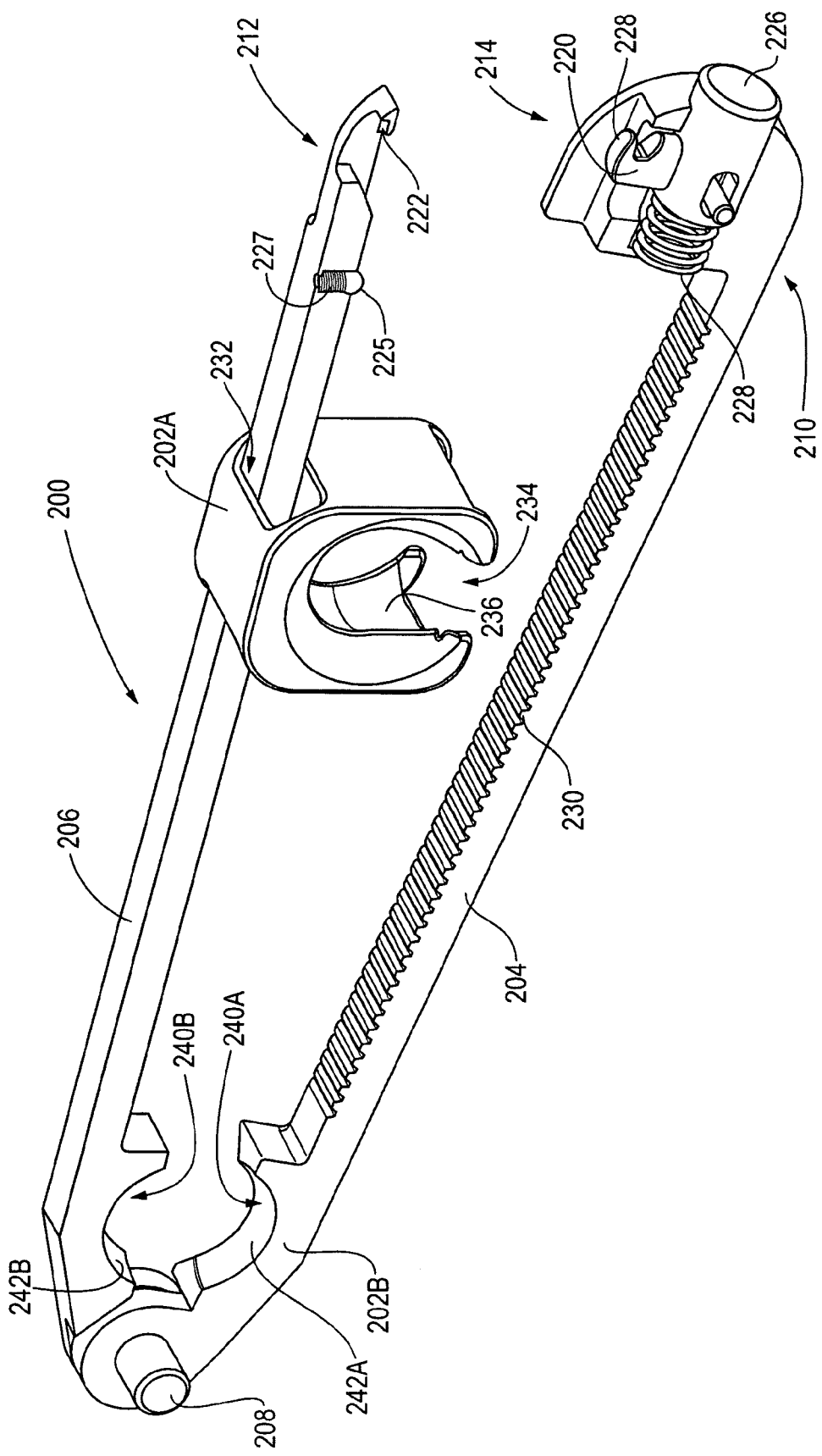
FIG. 8 is a partial cut away side view of the connector of FIG. 7, illustrating the connector in an open position.
Figure 9:
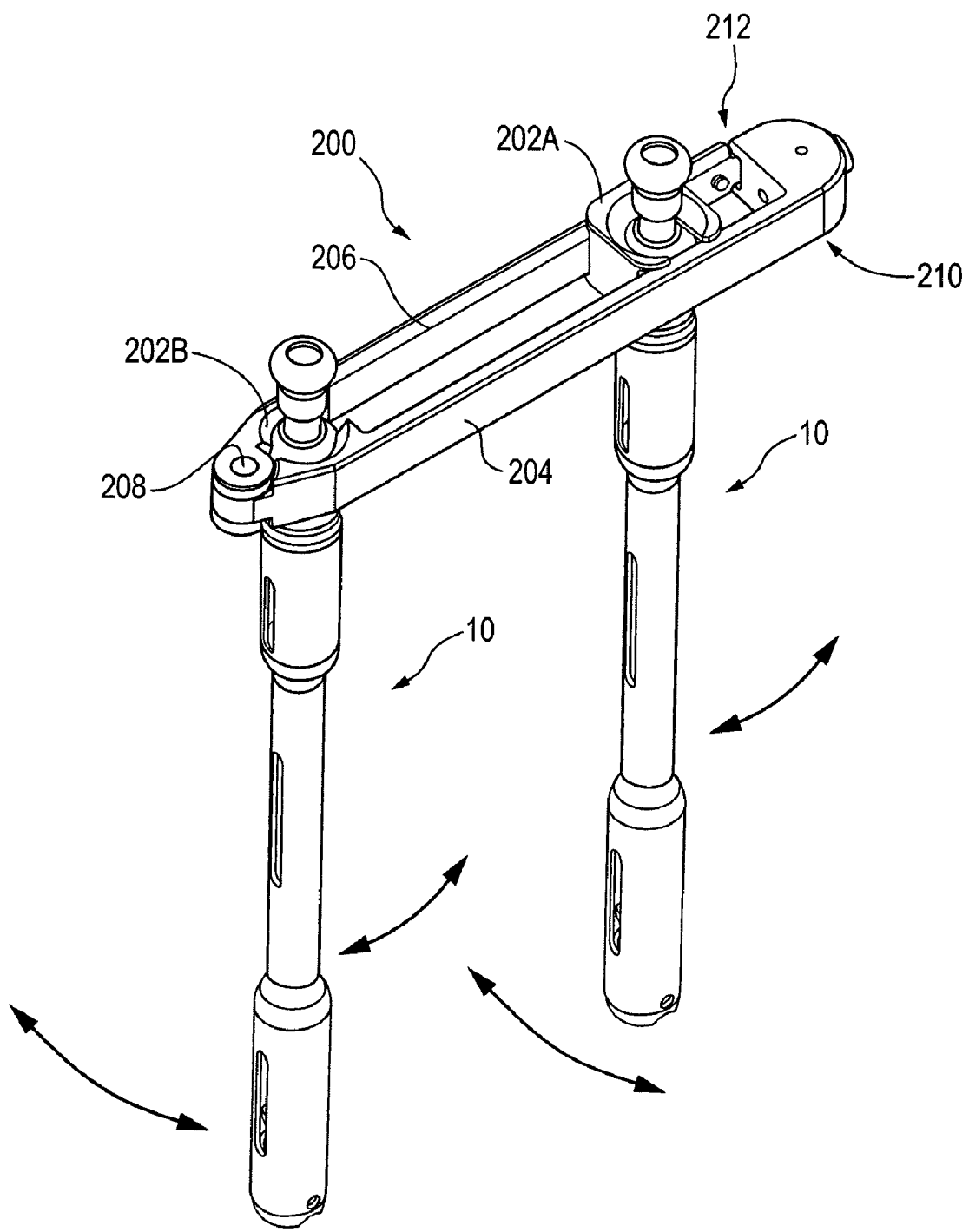
FIG. 9 is a perspective view of the connector of FIG. 7, illustrating the connector in the closed position and connecting two instruments such as the instrument of FIG. 1.
Figure 10:
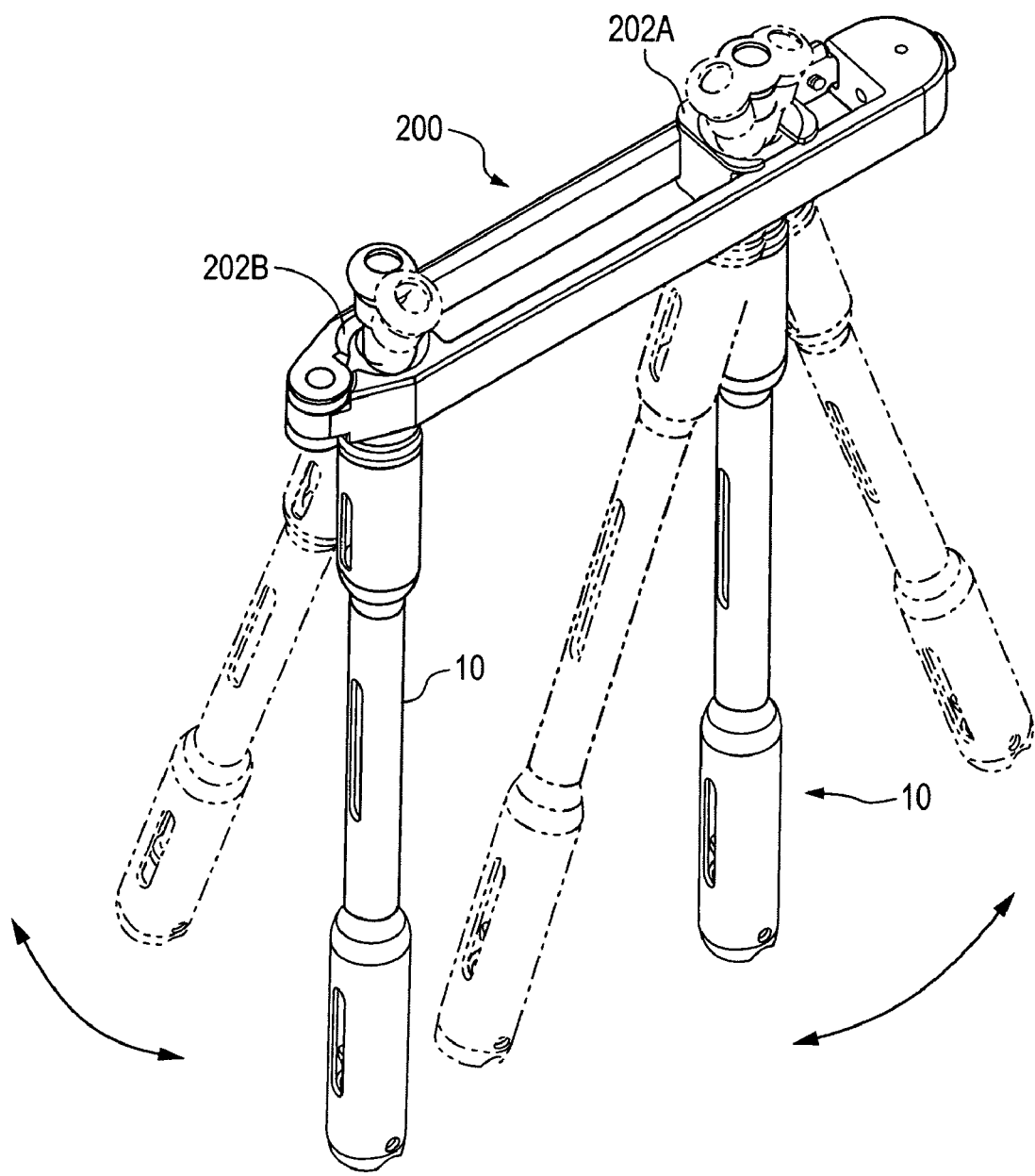
FIG. 10 is a perspective view of the connector of FIG. 7, illustrating the connector in the closed position and connecting two instruments such as the instrument of FIG. 1.

The exemplary connector 200 may include a first arm 204 pivotably connected to second arm 206 at a pivot point defined by a hinge pin 208. The exemplary connector 200 may be movable between an open position in which the first end 210 of the first arm 204 is separated from the first end 212 of the second arm 206, as illustrated in FIGS. 7 and 8, and a closed position in which the first end 210 of the first arm 204 is coupled to the first end 212 of the second arm 206, as illustrated in FIGS. 9 and 10. The open position facilitates connection of the instruments to the receiving elements 202 and adjustment of an adjustable receiving element, such as receiving element 202A. The exemplary connector 200 may include a latch mechanism 214 for selective coupling the first end 210 of the first arm 204 to the first end 212 of the second arm 206. In the exemplary embodiment, the latch mechanism 214 may include hook 220 positioned on the first arm 204 that may selectively engage a hook retaining element 222 positioned on the second arm 206. A cylindrically-shaped push button 226 is connected to the hook 222. Movement of the push button in a direction toward the hinge 208 causes the hook 220 to disengage from the hook retaining element 222 and, thus, releases the first arm 204 from the second arm 206. A spring 228 biases the push button 226 in a direction away from the hinge 208 and, thus, biases the hook 208 into an engagement position. The outer surface 228 of the hook 220 may be curved or angled to provide a camming surface that, when engaged by the bottom surface of the hook retaining element 222, causes the hook 220 to move from the engagement position toward the hinge 208, thus, allowing the hook 220 to engage the hook retaining element 222.

The first and/or second arm 204/206 may include a retaining member for retaining the adjustable receiving elements 202 on the arms when the connector is in the open position. For example, the second arm 206 of the exemplary connector 200 includes a retaining pin 225 for retaining the first receiving element 202A on the second arm 206. The retaining pin 225 may be adjusted along it is axis between an extended position in which the pin 225 impedes motion of the receiving element along the arm 206 and retracted position that facilitates removal and placement of the receiving element 202 on the arm 206. A spring 227 may be provided to bias the pin 225 to the extended position.

The first receiving element 202A, in the exemplary embodiment, includes a slot 232 for receiving the second arm 206 and permitting motion of the first receiving element 202A relative to the second arm 206 and other receiving elements, such as the second receiving element 202B. In the exemplary embodiment, the first arm 204 includes a plurality of teeth 230 for engaging a plurality of teeth on one or more of the receiving elements, for example, the first receiving element 202A, when the connector 200 is in the closed position. The engagement of the teeth 230 with teeth provided on an adjustable receiving element, for example, the adjustable receiving element 202A, may inhibit motion of the adjustable receiving element, thereby fixing the adjustable receiving element in position relative to the first arm 204, the second arm 206, and the other receiving elements.

The first receiving element 202A is generally C-shaped having an opening 234 to facilitate positioning of an instrument within the receiving element 202A. The first arm 204 may be positioned across the opening 234 when the connector is in the closed position to retain the instrument in the first receiving element 202A. The first receiving element 202A may be configured to permit polyaxial motion of an instrument relative to the receiving element 202A and, thus, the connector 200. For example, the first receiving element 202A may include a partially spherically shaped surface 236 that defines a seat or engagement surface for the connection element of the instrument, for example, the partially spherically shaped connection element 80 of the exemplary instrument 10, described above. The instrument 10, when connected to the first receiving element 202A of the connector 200, may be moved in a plurality of directions, for example, perpendicular to, parallel to, and about the axis of the instrument 10, as illustrated in FIGS. 9 and 10.

The second receiving element 202B, in the exemplary embodiment, may be defined by a first arcuate surface 240A provided on the first arm 204 and a second arcuate surface 240B provided on the second arm 206. The first arcuate surface 240A may be spaced apart from the second arcuate surface 240B when the connector 200 is in the open position, as illustrated in FIGS. 7 and 8, to facilitate positioning of an instrument within the second receiving element 202B. When the connector 200 is in the closed position, as illustrated in FIGS. 9 and 10, the first arcuate surface 240A and the second arcuate surface 240B are spaced apart a distance sufficient to retain the instrument within the second receiving element 202B. The second receiving element 202B, like the first receiving element 202A, may be configured to permit polyaxial motion of an instrument relative to the receiving element 202B and, thus, the connector 200. For example, the first arcuate surface 240A and the second arcuate surface 240B may each have a partially spherically shaped surface 242A, 242B that cooperatively define a seat or engagement surface for the connection element of the instrument, for example, the partially spherically shaped connection element 80 of the exemplary instrument 10, described above. The instrument 10, when connected to the second receiving element 202B of the connector 200, may be moved in a plurality of directions, for example, perpendicular to, parallel to, and about the axis of the instrument 10, as illustrated in FIGS. 9 and 10.

While the exemplary embodiment of the connector 200 is described and illustrated as having two receiving elements, the number and type (i.e., fixed or adjustable) of receiving elements may be varied to accommodate the number of instruments desired to be connected. For example, the exemplary connector 200 illustrated in FIGS. 12 and 13 includes three receiving elements—a fixed receiving element and two adjustable receiving elements.

Figure 11:
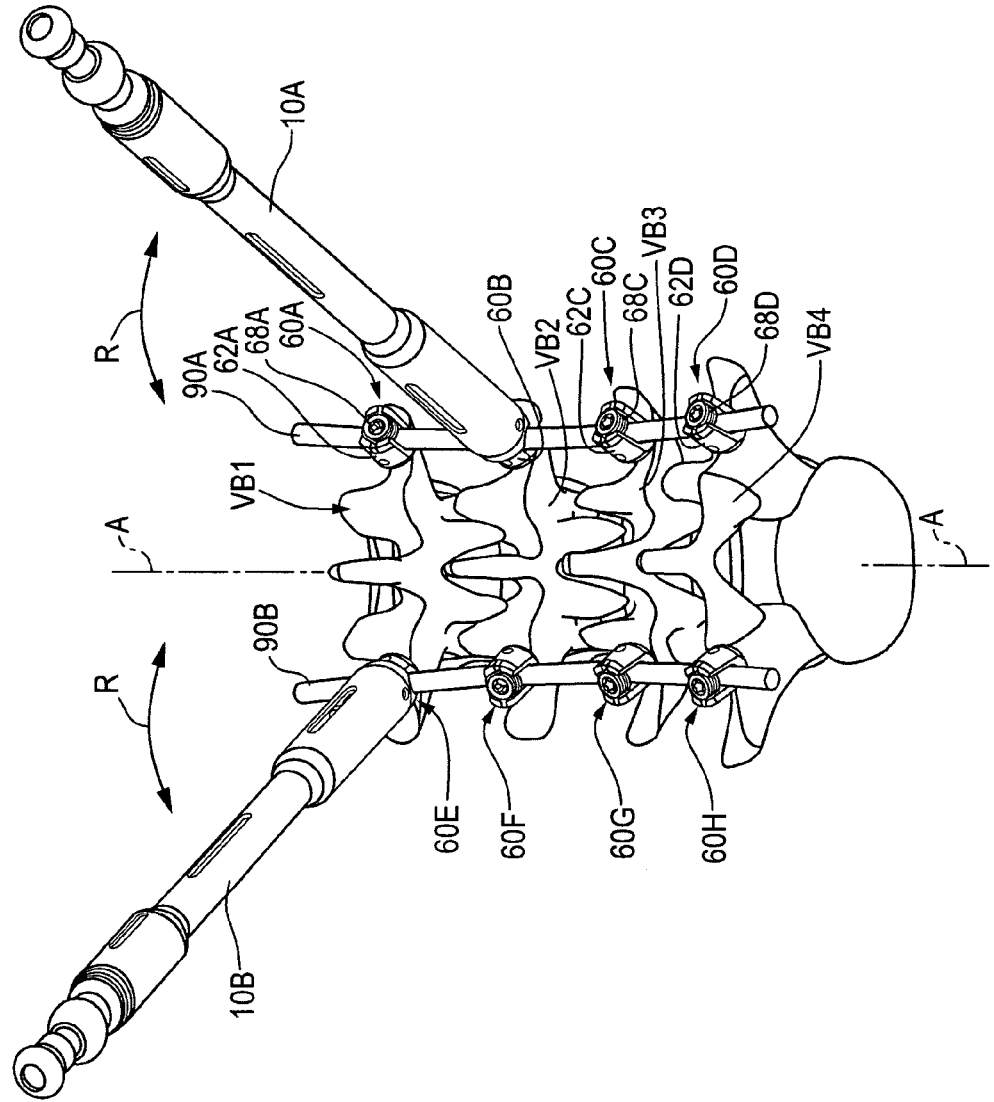
FIG. 11 is a perspective view of a first instrument connected to a first bone anchor engaged to a first vertebra and a second instrument connected to a second bone anchor engaged to a second vertebra, illustrating a method of adjusting the first vertebra relative to the second vertebra.

The exemplary instrument 10 may be employed to manipulate a bone anchor and the vertebra in which the bone anchor is implanted. In one exemplary method of manipulating a vertebra, the instrument 10 may be coupled to the receiving member or other portion of a bone anchor. Referring to FIG. 11, for example, a first instrument 10A may be coupled to the receiving member 62 of a bone anchor 60.

In the exemplary method, a spinal construct including a plurality of bone anchors implanted in a plurality of vertebra and a spinal rod connecting the bone anchors may be positioned in advance of using the first instrument to manipulate a vertebra. For example, a first bone anchor 60A may be connected to a first vertebra VB1, a second bone anchor 60B may be connected to a second vertebra VB2, a third bone anchor 60C may be connected to a third vertebra VB3, and a fourth vertebra 60D may be connected to a fourth vertebra VB4. In the exemplary method, the first, second, third, and fourth vertebrae are adjacent one another. In other exemplary methods, the bone anchors may be connected to non-adjacent vertebra to create the spinal construct. The bone anchors may be implanted into any suitable portion of the vertebrae. In the exemplary method, for example, each bone anchor is implanted into a pedicle of the vertebra.

A spinal rod 90A may be positioned relative to the bone anchors. For example, the spinal rod may be positioned in the receiving member 62 of each bone anchor 60. In the exemplary method, a closure mechanism, such as, for example, an inner set screw 68 may be positioned in the receiving member 62 of the bone anchors 60 to retain the spinal rod relative to the bone anchor.

In certain exemplary embodiments, a second construct may be positioned on the contra-lateral side of the spine from the first construct. In the exemplary method, a fifth bone anchor 60E is connected to the first vertebra VB1 opposite the first bone anchor 60A, a sixth bone anchor 60F is connected to the second vertebra VB2 opposite the second bone anchor 60B, a seventh bone anchor 60F is connected to the third vertebra VB3 opposite the third bone anchor 60C, and an eighth bone anchor 60G is connected to the fourth vertebra VB4 opposite the fourth bone anchor 60D. A second spinal rod 90B may be connected to the bone anchors 60E-G.

One skilled in the art will appreciate that the constructs illustrated in the FIGURES are exemplary constructs for facilitating the description of the use of the instruments and methods described herein. Other constructs employing the same or different bone anchors and fixation elements may be employed without departing from the scope of the present invention.

After connecting the first instrument 10A, the first instrument 10A may be manipulated to maneuver the second bone anchor 60B and the second vertebra VB2 relative to the first vertebra VB1, third vertebra VB3, and the fourth vertebra VB4. For example, the first instrument 10A may be moved a direction about the axis A of the spine, as indicated by arrow R in FIG. 11, to rotate the second vertebra VB2 about the axis A of the spine. Moreover, the instrument 10 may be used to maneuver the second bone anchor 60B and the second vertebra VB2 in any direction.

In the exemplary method, a second instrument 10B may be connected to the fifth bone anchor 60E, which is connected to the first vertebra VB1. The second instrument 10B and the first instrument 10A may be manipulated to maneuver the first vertebra VB1 and the second vertebra VB2 relative to one another. For example, the first instrument 10A may be rotated about the axis A of the spine to rotate the second vertebra VB2 about the spine and the second instrument 10B may be rotated about the axis A of the spine to rotate the first vertebra VB1 about the axis A of the spine. The first instrument 10A and the second instrument 10B may provide counter-torque to one another to facilitate motion of the first and second vertebrae. For example, the first instrument 10A and the second instrument 10B may be rotated in opposite directions about the axis A of the spine to facilitate correction of the angular orientation of the second vertebra VB2 and the first vertebra VB1.

In the exemplary method, a driver instrument may be inserted through the lumen 22 of the inner shaft 12 of the first instrument 10 to effect tightening of the closure mechanism 68B of the second bone anchor 60B. For example, a screw driver or the like may be advanced into engagement with the set screw of the bone anchor and may be manipulated to tighten the set screw to restrict motion of the spinal rod 90A relative to bone anchor 60B. In the exemplary method, the closure mechanism may be tightened after the angular orientation/position of the vertebra is adjusted by the first instrument 10A.

Figure 12:
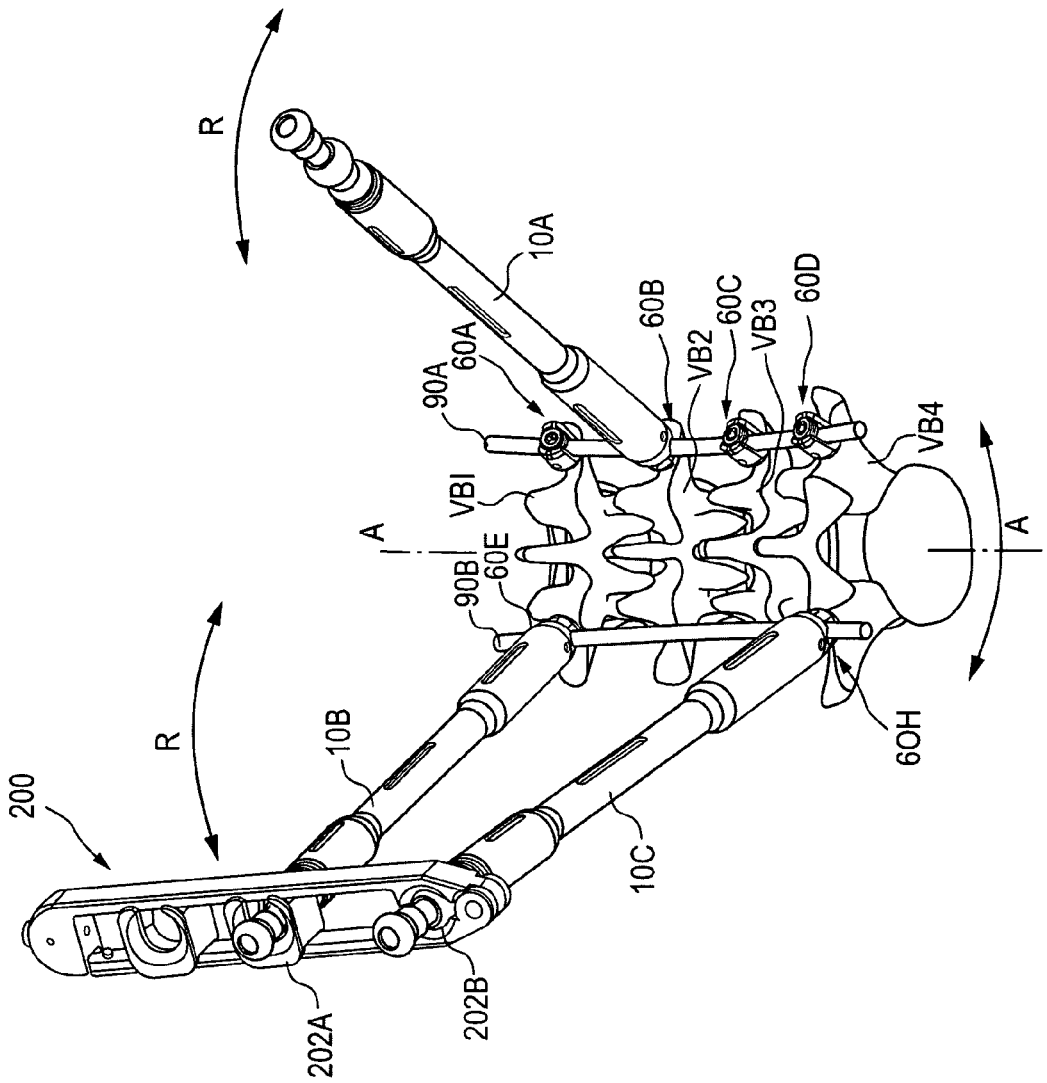
FIGS. 12 and 13 are perspective views of a connector connecting a first instrument to a second instrument, illustrating a method of adjusting a first and third vertebra relative to a second vertebra.
Figure 13:
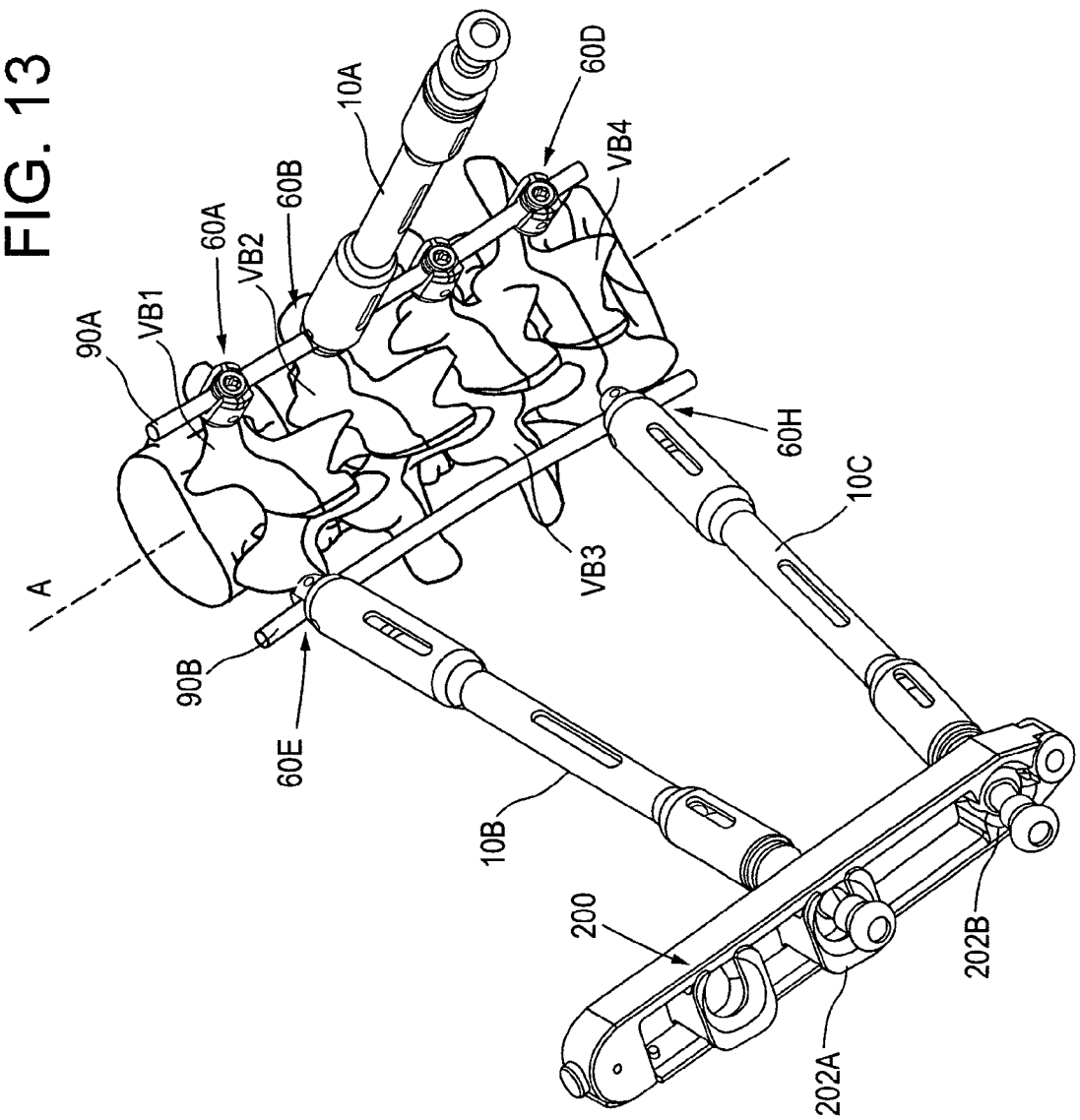

FIGS. 12 and 13 illustrate an exemplary method for manipulating a plurality of vertebrae. In the exemplary method, a first instrument 10A may be connected to a bone anchor 60B connected to a second vertebra. In addition, a second instrument 10B may be connected to a bone anchor 60E connected to a first vertebra and a third instrument 10C may be connected to a bone anchor 60H connected to a fourth vertebra VB4. The second and third instruments 10B, 10C may be connected by a connector, such as the connector 200 described above. After connecting the second and third instruments 10B, 10C to the respective bone anchor, the first receiving element 202A may be adjusted relative to the second receiving element 202B to facilitate connection of the second instrument 10B to the first receiving element 202A and the third instrument 10B to the second receiving element 202B. The connector 200 may be moved to manipulate the second instrument 10B and the third instrument 10C to rotate the first vertebra VB1 and the fourth vertebra VB4 relative to one another. For example, the connector 200 may be rotated in a direction indicated by arrow R about the axis A to rotate the first vertebra VB1 and the fourth vertebra VB2 about the axis A of the spine and relative to the second vertebra VB2 and the third vertebra VB3. Moreover, the first instrument 10A may be rotated in cooperation with the connector 200 to rotate the second vertebra VB2 about the axis A of the spine. The connector 200, and the second instrument 10B and third instrument 10C connected thereto, and the first instrument 10B may provide counter torque to one another. For example, the connector 200 and the first instrument 10A may be rotated in opposite directions about the axis A of the spine to facilitate correction of the angular orientation of the first vertebra VB1, the second vertebra VB2, and the fourth vertebra VB4.

Figure 14:
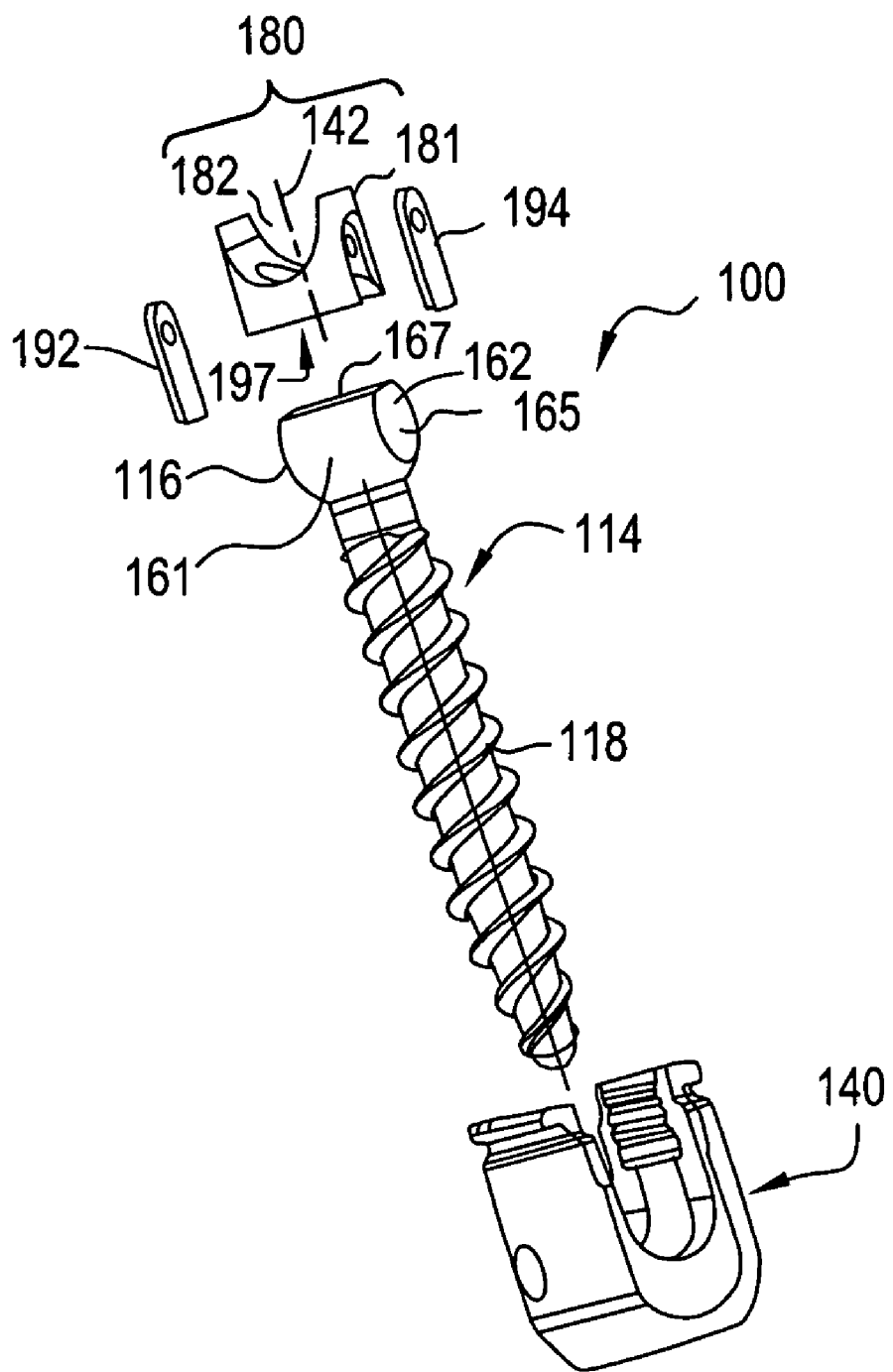
FIG. 14 is an exploded perspective view of the receiving member of a bone anchor in which the receiving member is adjustable relative to the bone engaging shaft of the bone anchor in a first direction and restricted from motion in a second direction.

The exemplary instruments described here in may be used with any type of bone anchor including, for example, a monoaxial bone screw, a polyaxial screw, or a hook. FIGS. 14-16 illustrates an exemplary embodiment of a bone screw 100 having a receiving member 140 that is adjustable relative to the bone engaging shaft 114 of the bone anchor 100 in a first direction and restricted from motion in a second direction. A compression and restriction member 180 for seating the head 116 of the bone engaging shaft 114 within the rod receiving member 140 includes restriction protrusions 192, 194 or other suitable mechanisms for selectively limiting the movement of the bone engaging shaft 114 relative to the receiving member 140. Such a bone anchor is described in detail in U.S. patent application Ser. No. 11/073,325, filed concurrently herewith, entitled Constrained motion Screw Assembly, incorporated herein by reference.

The bone engaging shaft 114 may include one or more bone engagement mechanisms, such as, for example, an external thread 118. The receiving member 140 receives the proximal head 116 of the bone anchor to couple the bone anchor 114 thereto, thereby coupling the bone to a rod or other element received in the rod-receiving member 140. In a rest position, the longitudinal axis 122 of the bone anchor aligns with a longitudinal axis 142 extending through the receiving member 140. The bone engaging shaft 114 is pivotable relative to the receiving member 140 about the proximal head 116 in one or more selected directions to angulate the longitudinal axis 122 relative to the longitudinal axis 142. The bone anchor 100 further includes one or more components, illustrated as the compression and restriction member 180, for preventing a pivoting movement of the bone engaging shaft 114 in one or more directions, so that the bone engaging shaft 114 cannot pivot in all 360 degrees around the receiving member 140, thereby increasing the stability of the screw assembly in one or more planes. For example, referring to FIGS. 15 and 16, the shaft is pivotable about axis T-T, but constrained from pivoting about axis R-R. Axis R-R is aligned with and parallel to the longitudinal axis r-r of the rod 12 in a selected plane and perpendicular to axis T-T, intersecting T-T at pivot point P, and may be substantially parallel to the longitudinal axis r-r of a rod to be received in the receiving portion 140.

The anchor head 116 of the bone engaging shaft 114 may be configured to facilitate controlled adjustment of the bone engaging shaft 114 relative to the receiving member 140 of the bone screw assembly. For example, the illustrative anchor head 116 may be substantially spherical and include curved side surfaces 161, 162 that are shaped to permit pivoting of the bone engaging shaft 114 relative to the receiving member 140 in one or more selected directions. The curved side surfaces 161, 162 are preferably curved in three-dimensions to facilitate rotation of the bone engaging shaft 114 relative to the receiving member 140. The illustrative anchor head 116 further includes two opposed flat side surfaces 163, 165 for constraining the pivoting movement to the one or more selected directions. The flat surfaces 163,165 preferably extend substantially parallel to the longitudinal axis 122 of the shaft 114. While the illustrative embodiment shows two opposed flat side surfaces 163, 165, one skilled in the art will recognize that the head can have any suitable number of flat surfaces or other selected feature for limiting the path of the shaft 114 relative to the receiving portion 140 about any selected axis or axes. The top surface 167 of the anchor head 116 may be a generally planar surface to facilitate seating of the anchor within the rod-receiving portion 140 of the screw assembly. The anchor head 116 may also have surface texturing, knurling and/or ridges.

The illustrative bone screw 100 further includes a compression and restriction member 180 for seating the anchor head 116 within the rod-receiving portion 140 of the screw 100 and for cooperating with the flat surfaces 163, 165 to constrain the movement of the anchor portion relative to the rod-receiving portion 140. The compression and restriction member 180 preferably forms a proximal rod seat 182 for seating a rod or other spinal fixation element and an opposed distal anchor seat 197 for engaging the anchor head 116. The illustrative compression and restriction member 180 includes a cap 181 and restricting protrusions 192, 194 that extend from a lower surface 184 of the cap 181. The restricting protrusions 192, 194 form a track-like region 197 for receiving the anchor head 116 therebetween. The restricting protrusions 192, 194 are configured to mate with the flat surfaces 163, 165 of the anchor head 116 when the bone screw 100 is assembled to guide and constrain the pivoting movement of the anchor head 116 relative to the receiving member 140. The illustrative restricting protrusions 192, 194 restrict movement of the anchor head 116 about axis T-T through a plane that is parallel to the flat faces 163, 165 of the proximal head 116 and the protrusions 192, 194.

In illustrative embodiment, the plane through which the bone engaging shaft 114 pivots is preferably defined by the longitudinal axis r-r of a rod inserted in the receiving member 140 when the bone screw 100 is assembled and the longitudinal axis 142 of the receiving member 142. However, one skilled in the art will recognize that the screw 100 may also be made to pivot in one or more other directions relative to the rod-receiving member 140.

The illustrated bone screw 100 facilitates positioning of the spinal rod 12 relative to the receiver member 140 by permitting the receiver member 140 to pivot relative to the shaft 114 about axis T-T, (e.g., the receiver member 140 is movable in the sagittal plane). Moreover, the illustrated bone screw 100 facilitates adjustment of the angular orientation of the vertebra in which the bone screw is implanted by an instrument connected to the bone anchor 100, such as the exemplary instrument 10 described above. For example, the bone screw 100 provides stability in the transverse plane by restricting pivoting of the receiver member 140 about the axis R-R. The stability of the bone screw in the transverse plane facilitates movement of the bone screw 100 and vertebra in the transverse plane, e.g., facilitates rotation of the bone anchor 100 and the vertebra about axis R-R.

FIGS. 17A & 17B illustrate an alternative embodiment of an instrument 210 for manipulating a vertebra. The exemplary instrument 210 includes an elongate shaft 212 including a pair of fingers 250A, 250B positioned at the distal end of the shaft 212. A first finger 250A is movable relative to a second finger 50B to allow the fingers 250A, 250B to capture a portion of a bone anchor 60 there-between. In the exemplary embodiment, for example, the first finger 250A may be pivotably connected by a hinge 251 to the shaft 212 and the second finger 250B is integral to the shaft 212. The first finger 250A is movable between a first position, illustrated in FIG. 17A, in which the first finger 250A is spaced apart from the second finger 250B to allow the fingers 250A, 250B to receive a portion of a bone anchor 60 there-between, and a second position, illustrated in FIG. 17B, in which the first finger 250A is proximate the second FIG. 250B to retain the portion of bone anchor between the fingers 250A,B.

A lever arm 261 or other actuation mechanism may be coupled to the first finger 250A to facilitate movement of the first finger 250A between the first and second position. The lever arm 261, in the exemplary embodiment, is coupled to the first finger 250A through a plurality of pivot points, e.g. hinges 251, 253, 258. The lever arm 261 may be moved towards or away from the shaft 212 to move the first finger 250A between the first and second positions. A leaf spring 263, or other spring, may be provided to bias the lever arm 261 away from the shaft 212, as illustrated in FIG. 17A. A latch 265 may be provided at the proximal end of the shaft 212 to selectively retain the lever arm 261 in contact with the shaft 212, as illustrated in FIG. 17B.

While the instruments and methods of the present invention have been particularly shown and described with reference to the exemplary embodiments thereof, those of ordinary skill in the art will understand that various changes may be made in the form and details herein without departing from the spirit and scope of the present invention. Those of ordinary skill in the art will recognize or be able to ascertain many equivalents to the exemplary embodiments described specifically herein by using no more than routine experimentation. Such equivalents are intended to be encompassed by the scope of the present invention and the appended claims.

What is claimed as new and desired to be protected by Letters Patent of the United States is:

1. A system for manipulating one or more vertebra, the system comprising:
    a first instrument having a distal end configured to engage a first bone anchor connected to a first vertebra,
    a second instrument having a distal end configured to engage a second bone anchor connected to a second vertebra, and
    a connector connecting the first instrument and the second instrument, the connector including:
        a first arm substantially extending along a first axis and having a first end and a second end,
        a second arm substantially extending along a second axis and having a first end and a second end,
        a first receiving element for receiving the first instrument, the first receiving element being disposed between the first arm and the second arm, and
        a second receiving element for receiving the second instrument, the second receiving element being disposed between the first arm and the second arm, the first receiving element being movable along the first arm so that a position of the first receiving element along the first arm is adjustable relative to the second receiving element,
        wherein the second end of the first arm is pivotably connected to the second end of the second arm, the first and second arms being movable between an open position in which the first end of the first arm is separated from the first end of the second arm and a closed position in which the first end of the first arm is coupled to the first end of the second arm.

2. The system of claim 1, wherein the first instrument is angularly adjustable relative to the first receiving member.

3. The system of claim 2, wherein the second instrument is angularly adjustable relative to the second receiving member.

4. The system of claim 1, wherein the second receiving element is fixed in position relative to the first arm and the second arm.

5. The system of claim 1, wherein connector further comprises a retaining pin for retaining the first receiving element on the first arm, the retaining pin being adjusted between an extended position where the pin impedes motion of the first receiving element along the first arm and an retracted position where removal and placement of the first receiving element on the first arm is facilitated.

6. The system of claim 1, wherein the first receiving element comprises a slot for receiving the first arm and permitting motion of the first receiving element along the first arm.

7. The system of claim 1, wherein the first receiving element is C-shaped having an opening to facilitate positioning of the first instrument within the first receiving element.

8. The system of claim 1, wherein the first receiving element and the second receiving element are configured to allow polyaxial motion of the first instrument and the second instrument relative to the first receiving element and the second receiving element, respectively.

9. The system of claim 1, wherein the first receiving element comprises a partially spherically shaped surface that defines an engagement surface for the first instrument.

10. The system of claim 1, wherein the first instrument, when connected to the first receiving element, moves in a plurality of directions including directions perpendicular to, parallel to, and about an axis of the first instrument.

11. A system for manipulating one or more vertebra, the system comprising:
    a first instrument having a distal end configured to engage a first bone anchor connected to a first vertebra,
    a second instrument having a distal end configured to engage a second bone anchor connected to a second vertebra, and
    a connector connecting the first instrument and the second instrument, the connector including:
        a first arm substantially extending along a first axis and having a first end and a second end,
        a second arm substantially extending along a second axis and having a first end and a second end,
        a first receiving element for receiving the first instrument, the first receiving element being disposed between the first arm and the second arm, and
        a second receiving element for receiving the second instrument, the second receiving element being disposed between the first arm and the second arm, the first receiving element being movable along the first arm so that a position of the first receiving element along the first arm is adjustable relative to the second receiving element, wherein the connector further comprises a latch for coupling the first end of the first arm to the first end of the second arm.

12. A system for manipulating one or more vertebra, the system comprising:
    a first instrument having a distal end configured to engage a first bone anchor connected to a first vertebra,
    a second instrument having a distal end configured to engage a second bone anchor connected to a second vertebra, and
    a connector connecting the first instrument and the second instrument, the connector including:
        a first arm substantially extending along a first axis and having a first end and a second end,
        a second arm substantially extending along a second axis and having a first end and a second end,
        a first receiving element for receiving the first instrument, the first receiving element being disposed between the first arm and the second arm, and
        a second receiving element for receiving the second instrument, the second receiving element being disposed between the first arm and the second arm, the first receiving element being movable along the first arm so that a position of the first receiving element along the first arm is adjustable relative to the second receiving element, wherein the second arm includes a plurality of teeth for engaging the first receiving element.

13. The system of claim 12, wherein the first receiving element is fixed in position relative to the second receiving elements when the teeth on the second arm engage the first receiving element.

* * * * *

UNITED STATES PATENT AND TRADEMARK OFFICE
CERTIFICATE OF CORRECTION

| | |
|---|---|
| PATENT NO. | : 8,007,516 B2 |
| APPLICATION NO. | : 11/707471 |
| DATED | : August 30, 2011 |
| INVENTOR(S) | : Nam T. Chao et al. |

Page 1 of 1

It is certified that error appears in the above-identified patent and that said Letters Patent is hereby corrected as shown below:

Title Page, correct Item (75) Inventors, to read:

-- (75)    Inventors:    Nam T. Chao, Marlborough, MA (US);
Dennis Hubbard, Lancaster, MA (US);
Chris Rybicki, Fall River, MA (US);
Ronald Sacher, Needham, MA (US);
James R. Donahue, East Falmouth, MA (US); Simon Siu, Quincy, MA (US);
Randal Betz, Ocean City, NJ (US);
Peter O. Newton, San Diego, CA (US) --.

Signed and Sealed this
Thirteenth Day of January, 2015

Michelle K. Lee
*Deputy Director of the United States Patent and Trademark Office*